US012591094B2

(12) United States Patent (10) Patent No.: US 12,591,094 B2
Jia et al. (45) Date of Patent: Mar. 31, 2026

(54) OPTICAL DEVICE AND A METHOD OF FORMING AN OPTICAL DEVICE

(71) Applicant: Royal Melbourne Institute of Technology, Melbourne (AU)

(72) Inventors: Baohau Jia, Hawthorn (AU); Han Lin, Hawthorn (AU)

(73) Assignee: Royal Melbourne Institute of Technology, Melbourne (AU)

( * ) Notice: Subject to any disclaimer, the term of this patent is extended or adjusted under 35 U.S.C. 154(b) by 387 days.

(21) Appl. No.: 17/441,570

(22) PCT Filed: Mar. 20, 2020

(86) PCT No.: PCT/AU2020/050266
§ 371 (c)(1),
(2) Date: Sep. 21, 2021

(87) PCT Pub. No.: WO2020/191431
PCT Pub. Date: Oct. 1, 2020

(65) Prior Publication Data
US 2022/0175251 A1 Jun. 9, 2022

(30) Foreign Application Priority Data
Mar. 22, 2019 (AU) ................................ 2019900970

(51) Int. Cl.
*G02B 6/26* (2006.01)
*A61B 1/00* (2006.01)
(Continued)

(52) U.S. Cl.
CPC .......... *G02B 6/262* (2013.01); *A61B 1/00096* (2013.01); *A61B 1/00167* (2013.01);
(Continued)

(58) Field of Classification Search
CPC ................ G02B 6/262; G02B 6/02061; G02B 2006/0098; G02B 26/103; G02B 3/08;
(Continued)

(56) References Cited

U.S. PATENT DOCUMENTS 4,815,807 A * 3/1989 Kaneko ..................... G02B 6/32
385/33
5,031,991 A * 7/1991 Nakatsu ............... G02B 6/4206
385/33
(Continued)

FOREIGN PATENT DOCUMENTS

CN        101717203  B   *  9/2011
JP        62062306  A   *  3/1987  ........... G02B 6/4203
(Continued)

OTHER PUBLICATIONS

Modell et al. ("Fiber Optics in Medicine", Encyclopedia of Medical Devices and Instrumentation, Second Edition, 2006, John Wiley & Sons, Inc, pp. 301-315) (Year: 2006).*
(Continued)

*Primary Examiner* — Michelle R Connelly
(74) *Attorney, Agent, or Firm* — Withrow + Terranova, PLLC; Vincent K. Gustafson

(57) ABSTRACT

Described herein is an optical device that is arranged to emit electromagnetic radiation and a method of forming an optical device. In one embodiment, the optical device comprises an optical fibre that is arranged to transmit electromagnetic radiation between a source of electromagnetic radiation and an area of interest of a sample material. The optical device also comprises an optical element coupled to an end portion of the optical fibre. The optical element comprises a graphene lens that is arranged to focus the (Continued)

electromagnetic radiation transmitted by the optical fibre to a focal region within the area of interest of the sample material.

21 Claims, 24 Drawing Sheets

(51) Int. Cl.

| | |
|---|---|
| *A61B 1/07* | (2006.01) |
| *A61B 5/00* | (2006.01) |
| *C01B 32/184* | (2017.01) |
| *C01B 32/192* | (2017.01) |
| *C01B 32/198* | (2017.01) |
| *G02B 3/08* | (2006.01) |
| *G02B 6/02* | (2006.01) |
| *G02B 6/32* | (2006.01) |
| *G02B 23/24* | (2006.01) |
| *G02B 23/26* | (2006.01) |
| *G02B 26/10* | (2006.01) |
| *G02F 1/01* | (2006.01) |

(52) U.S. Cl.
CPC ............ *A61B 1/00188* (2013.01); *A61B 1/07* (2013.01); *A61B 5/0066* (2013.01); *A61B 5/0084* (2013.01); *C01B 32/184* (2017.08); *C01B 32/192* (2017.08); *C01B 32/198* (2017.08); *G02B 3/08* (2013.01); *G02B 6/02061* (2013.01); *G02B 23/2423* (2013.01); *G02B 23/26* (2013.01); *G02B 26/10* (2013.01); *G02F 1/0102* (2013.01); *A61B 2562/0233* (2013.01); *A61B 2562/12* (2013.01); *C01P 2004/03* (2013.01); *C01P 2004/04* (2013.01); *G02B 6/32* (2013.01); *G02F 2201/02* (2013.01); *G02F 2203/12* (2013.01); *G02F 2203/50* (2013.01)

(58) Field of Classification Search
CPC ...... G02B 6/34; G02B 23/2423; G02B 23/26; G02B 26/10; G02B 6/32; G02B 6/04; G02B 1/002; G02B 6/10; G02B 6/43; A61B 1/00096; A61B 5/0066; A61B 1/00172; A61B 1/00188; A61B 1/07; A61B 2562/0233; A61B 2562/0238; A61B 2562/0242; A61B 1/00167; A61B 1/00165; A61B 5/0084; A61B 2562/12; A61B 5/0071; A61B 5/742; A61B 2560/0406; A61B 2562/185; A61B 2562/223; C01B 32/184; C01B 32/192; C01B 32/198; G02F 1/0102; G02F 2201/02; G02F 2203/12; G02F 2203/50; C01P 2004/03; C01P 2004/04; C01P 2006/60

See application file for complete search history.

(56) References Cited

U.S. PATENT DOCUMENTS

| | | | |
|---|---|---|---|
| 6,488,414 B1 * | 12/2002 | Dawes ............... | G02B 6/02061 |
| | | | 977/827 |
| 7,728,985 B2 * | 6/2010 | Feldchtein .......... | A61B 5/0066 |
| | | | 356/497 |
| 2009/0202202 A1 * | 8/2009 | Lee .................. | B29D 11/00663 |
| | | | 385/33 |
| 2011/0188805 A1 * | 8/2011 | Fu ............................ | G02B 6/34 |
| | | | 156/60 |
| 2013/0137944 A1 | 5/2013 | Jeong et al. | |
| 2017/0310889 A1 * | 10/2017 | Seibel ................. | H04N 23/959 |

FOREIGN PATENT DOCUMENTS

| | | | | | |
|---|---|---|---|---|---|
| JP | 63033716 A | * | 2/1988 | ............... | G02B 6/32 |
| KR | 20080029598 A | * | 4/2008 | ....... | G02F 1/133504 |

OTHER PUBLICATIONS

Deng et al. ("Ultra-thin flat lenses made of Graphene", Proceedings of the 15th IEEE International Conference on Nanotechnology, Jul. 27-30, 2015, Rome Italy, pp. 132-135) (Year: 2015).*

Bowler ("New Graphene Lens Could Help Computers Beam Data at The Speed of Light", Science alert, TECH, Feb. 11, 2016, pp. 1-3) (Year: 2016).*

Zheng et al. ("Highly efficient and ultra-broadband graphene oxide ultrathin lenses with three-dimensional subwavelength focusing", Nature Communications, Sep. 22, 2015, Macmillan Publishers Limited, pp. 1-7) (Year: 2015).*

Peleg, Roni ("Graphene-based flat lenses", Feb. 17, 2015, Birmingham. ac.uk, https://www.graphene-info.com/graphene-based-flat-lenses) (Year: 2015).*

Kou et al. ("High-resolution imaging of graphene by tip-enhanced coherent anti-Stokes Raman scattering", Journal of Innovative Optical Health Sciences, vol. 12, No. 1 (2019), Jan. 23, 2019, pp. 1841003-1 to 1841003-7) (Year: 2019).*

Cao, Guiyuan ("On Fibre Tip Graphene-based Ultrathin Flat Lens Towards High-Resolution Endoscopes", Swineburn University of Technology, 2020, https://researchbank.swinburne.edu.au/file/20ddfd25-b538-4008-a913-3607b1438012/1/guiyuan_cao_thesis.pdf) (Year: 2020).*

Szondy, David ("Graphene optical lens a billionth of a meter thick breaks the diffraction limit", Jan. 21, 3016, New Atlas, https://newatlas.com/optical-lens-one-billionth-meter-thick/41588/, pp. 1-9) (Year: 2016).*

Cao et al. ("A fiber tip graphene oxide lens towards fiber optic endoscope application", Frontiers in Optics, Laser Science, OSA 2019, 2 pages) (Year: 2019).*

Gui et al., Machine Translation of CN-101717203-B, Sep. 28, 2011. (Year: 2011).*

Abe, Hiroshi et al., Machine Translation of JP 62-062306 A, Mar. 19, 1987. (Year: 1987).*

Ogata, Shiro et al., Machine Translation of JP 63-033716 A, Feb. 13, 1988. (Year: 1988).*

Yoon Shin Young, Machine Translation of KR 2008-0029598 A, Apr. 3, 2008. (Year: 2008).*

International Search Report (Form PCT/ISA/210) for International Application No. PCT/AU2020/050266 mailed Apr. 23, 2020, 4 pages.

Written Opinion (Form PCT/ISA/237) for International Application No. PCT/AU2020/050266 mailed Apr. 23, 2020, 5 pages.

Zheng X. et al., "Highly efficient and ultra-broadband graphene oxide ultrathin lenses with three-dimensional subwavelength focusing", Nat. Commun. 6, 8433, pp. 1-7, Sep. 22, 2015. https://doi.org/10.1038/ncomms9433.

Graphene Oxide Miniaturised Fibre Optics Endoscope [retrieved on Apr. 21, 2020]. Retrieved from the Internet: <URL: http:/acamma.com/project2graphene-oxide-miniaturised-fibre-optics-endoscope.html>, 2017, 2 pages.

Cao G., "An accurate design of graphene oxide ultrathin flat lens based on Rayleigh-Sommerfeld theory", Opto-Electronic Advances, vol. 1, No. 7, 18001201-18001207 (2018). DOI: 10.29026/oea.2018.180012.

Pahlevaninezhad H. et al., "Nano-optic endoscope for high-resolution optical coherence tomography in vivo", Nature Photon 12, 540-547 (2018). https://doi.org/10.1038/s41566-018-0224-2. (Abstract only.).

Gora M. et al., "Endoscopic optical coherence tomography: technologies and clinical applications [Invited]", Biomed Opt Express, vol. 8( 5), 2405-2444 (2017). DOI: 10.1364/BOE.8.002405.

Georgiou T. et al., "Graphene bubbles with controllable curvature", Applied Physics Letters 99, 093103, pp. 1-3 (2011). DOI: 10.1063/1.3631632.

(56) References Cited

OTHER PUBLICATIONS

Kong, X et al., "Graphene-based ultrathin flat lenses", ACS Photonics, vol. 2(2) pp. 200-207, (2015). http://dx.doi.org/ doi: 10.1021/ph500197j.

Graphene Oxide Miniaturised Fibre Optics Endoscope [retrieved on Apr. 21, 2020]. Retrieved from the Internet: <URL: https://web.archive.org/web/20171202055529/http://acamma.com/projects.html> Published Dec. 2, 2017 per Wayback Machine.

* cited by examiner

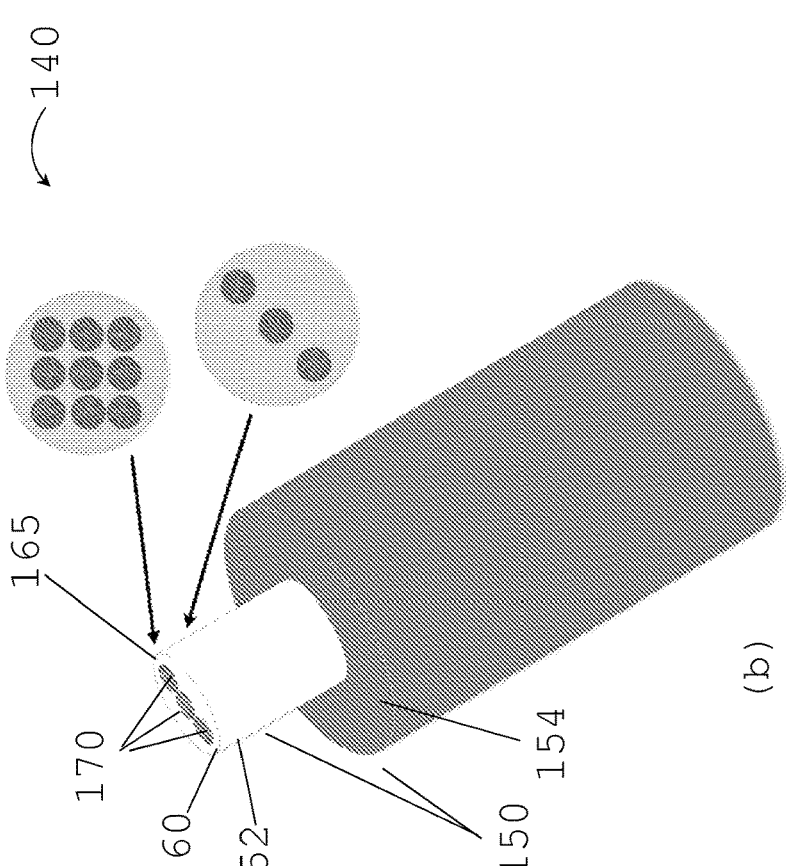
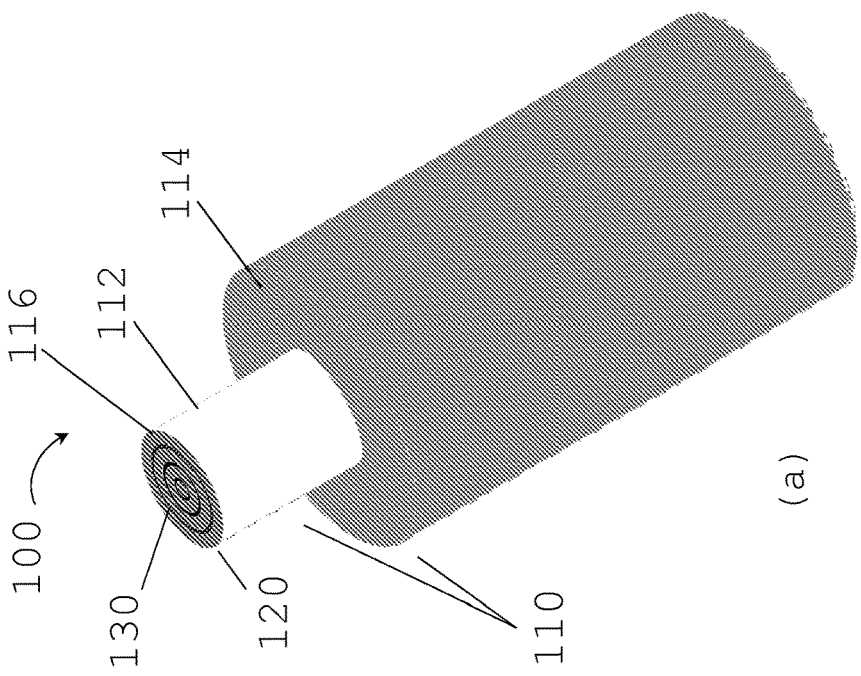
Figure 1

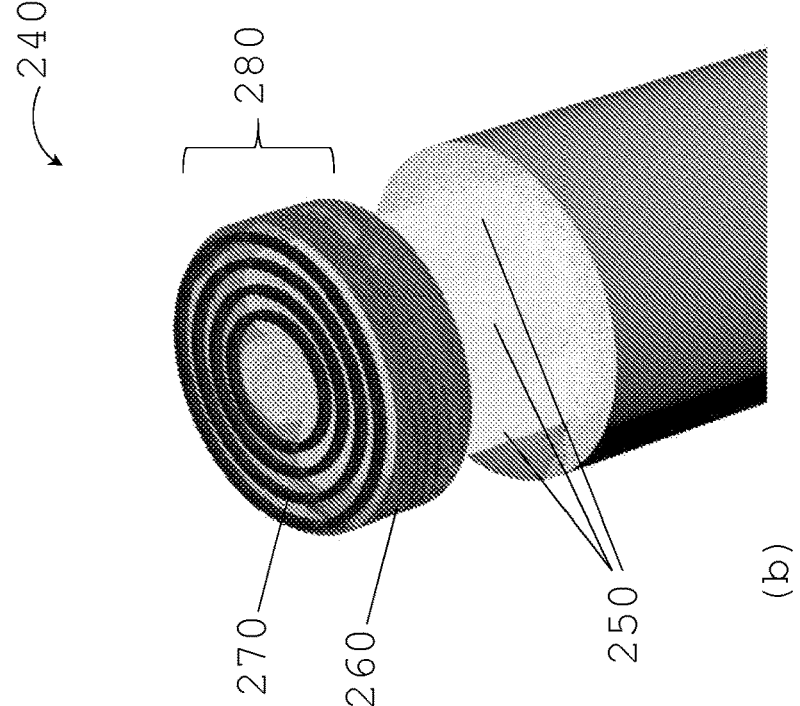
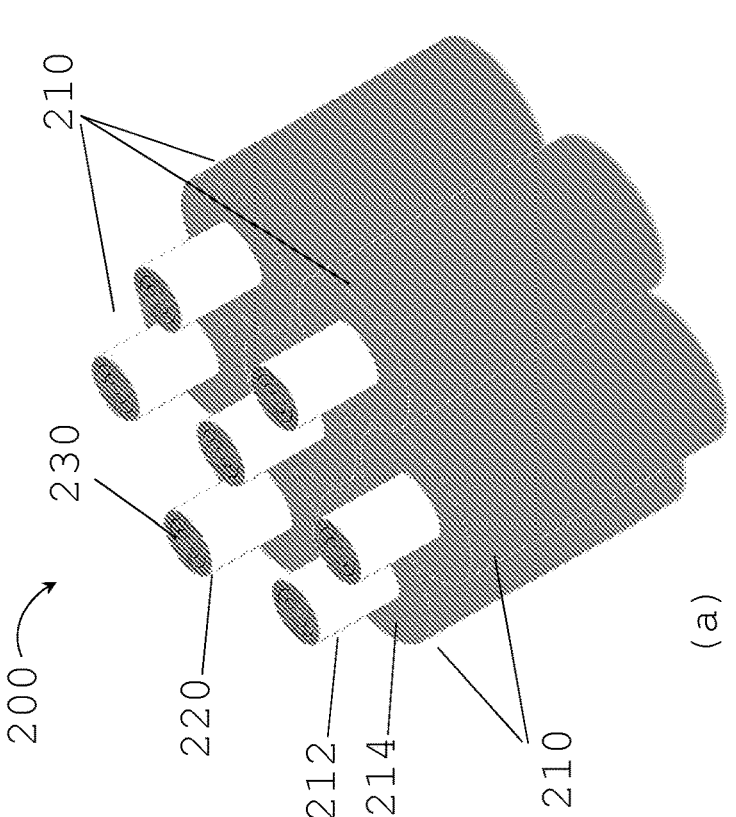
Figure 2

800

1500

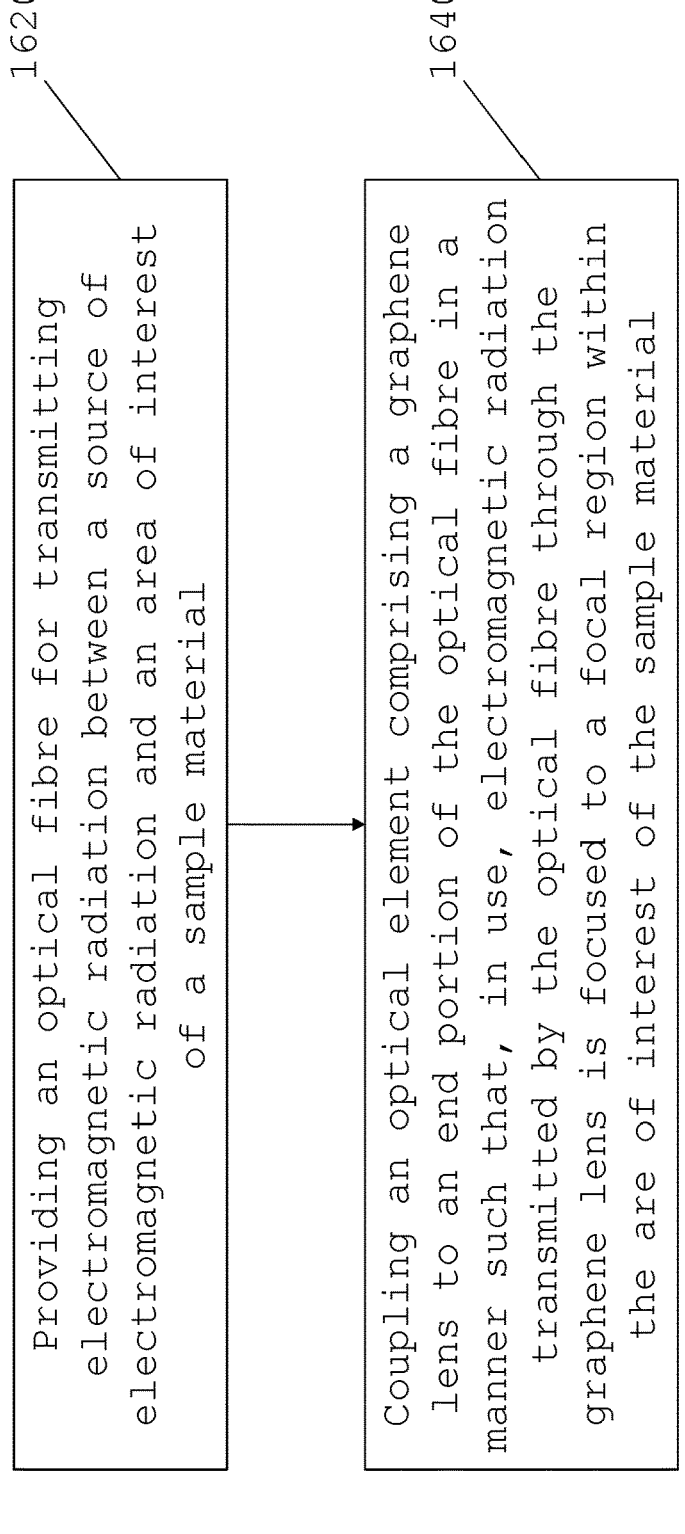

1620

Providing an optical fibre for transmitting electromagnetic radiation between a source of electromagnetic radiation and an area of interest of a sample material

1640

Coupling an optical element comprising a graphene lens to an end portion of the optical fibre in a manner such that, in use, electromagnetic radiation transmitted by the optical fibre through the graphene lens is focused to a focal region within the are of interest of the sample material

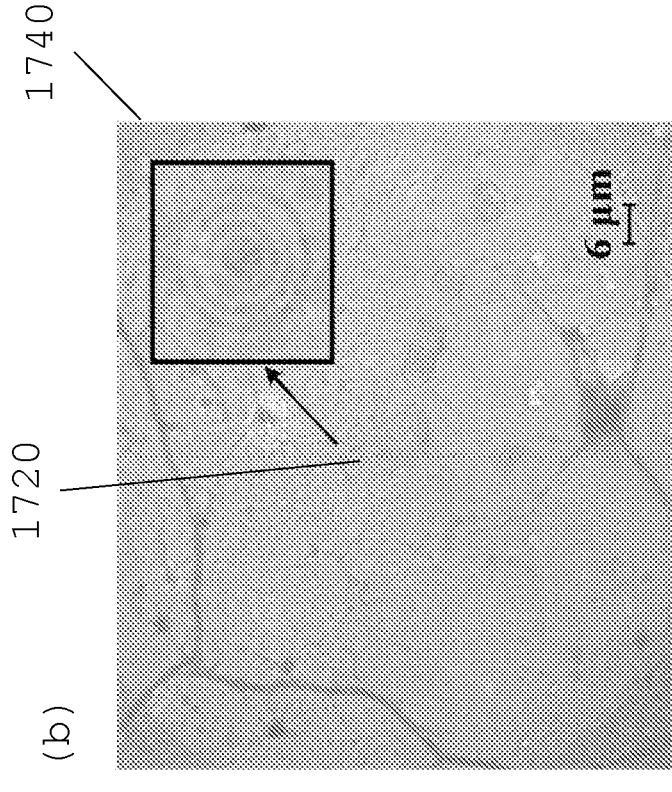
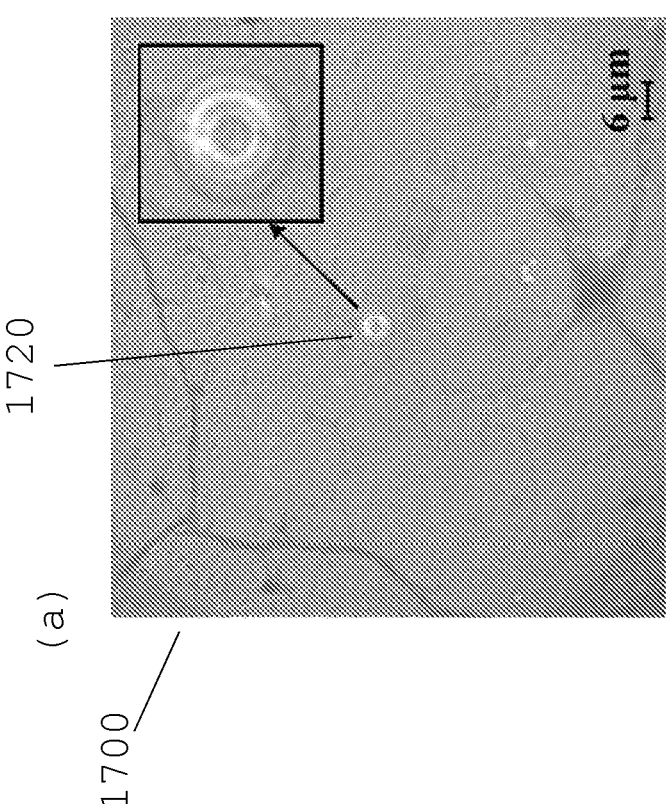
Figure 20

2140

2130

2120

2110

OPTICAL DEVICE AND A METHOD OF FORMING AN OPTICAL DEVICE

CROSS-REFERENCE TO RELATED APPLICATIONS

This application is a 35 U.S.C. § 371 national phase filing of International Application No. PCT/AU2020/050266 filed on Mar. 20, 2020 and claiming benefit of Australian Patent Application No. 2019900970 filed on Mar. 22, 2019, wherein the entire disclosures of the foregoing applications are hereby incorporated by reference herein.

TECHNICAL FIELD OF THE INVENTION

The present invention generally relates to an optical device and a method of forming an optical device, and relates particularly, though not exclusively, to an optical fibre endoscope and a method of forming the optical fibre endoscope.

BACKGROUND OF THE INVENTION

Optical devices such as optical fibre endoscopes or probes have a particular application in the medical field. Endoscopes can, for example, be inserted into a biological tissue or in a hollow organ or cavity of a body for medical examination. OCT using optical fibre probes is a non-invasive optical imaging technique that is used for imaging biological tissue and can be used for identifying diseased tissue and, for example, tumours during surgery.

Optical fibre probes used as endoscopes or for OCT measurements typically comprise optical elements, such as, for example, Graded-Index (GRIN) lenses, which contribute to the image resolution that optical fibre-based imaging techniques can achieve, as well as to the size of the optical fibre probes.

The image resolution and optical resolution provided by currently available optical fibre-based imaging techniques however remains relatively limited. Further, since optical fibre endoscopes may be inserted into the interior of a hollow organ or cavity of a body, it is desired to minimise the size of such optical fibre endoscopes such that the invasive aspect of the endoscopes as well as the risk of damage to surrounding biological tissue during insertion and examination can be minimised.

SUMMARY OF THE INVENTION

In accordance with a first aspect of the present invention, there is provided an optical device that is arranged to emit electromagnetic radiation, the optical device comprising:

an optical fibre that is arranged to transmit electromagnetic radiation between a source of electromagnetic radiation and an area of interest of a sample material; and an optical element coupled to an end portion of the optical fibre, the optical element comprising a graphene lens that is arranged to focus the electromagnetic radiation transmitted by the optical fibre to a focal region within the area of interest of the sample material.

The optical device may further be arranged to receive electromagnetic radiation that interacted with the area of interest of the sample material. In this embodiment, the optical element is arranged to receive electromagnetic radiation that interacted with the area of interest of the sample material and the optical fibre is further arranged to transmit the electromagnetic radiation received by the optical element.

The optical element may be formed directly or indirectly on the end-portion of the optical fibre. Alternatively, the optical element may be attached to the end-portion of the optical fibre.

The optical fibre may be a single-mode optical fibre.

Alternatively, the optical device may comprise a multi-mode optical fibre. The optical element may in this embodiment comprise at least two graphene lenses that are arranged to focus light transmitted by the optical fibre to at least two focal regions within the area of interest of the sample material. In another embodiment implementing a multi-mode optical fibre, the optical element comprises a single graphene lens.

In one embodiment, the optical fibre is one of a bundle of optical fibres and the optical element is one of a plurality of optical elements. In this embodiment each optical element may be positioned at an end-portion of a respective one of the bundle of optical fibres.

Alternatively, the optical device may comprise a bundle of optical fibres, the optical element being coupled to the end portions of the optical fibres of the bundle.

The graphene lens may be arranged to focus the electromagnetic radiation to the focal region with a sub-micron optical resolution.

In accordance with a second aspect of the present invention, there is provided an endoscope comprising the optical device of the first aspect of the present invention.

In accordance with a third aspect of the present invention, there is provided an optical coherence tomography system comprising the optical device of the first aspect of the present invention.

In accordance with a fourth aspect of the present invention, there is provided a scanning imaging system comprising:

the optical device of the first aspect of the present invention; and a scanning head coupled to, or comprising at least a portion of, the optical device, the scanning head being arranged for changing a position of the optical element of the optical device relative to the sample material such that the focal region within the area of interest can be scanned across the area of interest of the sample material.

In accordance with a fifth aspect of the present invention, there is provided a scanning imaging system comprising:

the optical device of the first aspect of the present invention wherein the optical fibre is a multi-mode fibre; and a spatial light modulator coupled to the optical device, the spatial light modulator being arranged for phase modulation of electromagnetic radiation transmitted through the optical fibre;

wherein the optical device is arranged to scan the focal region across the area of interest by phase modulation.

The scanning imaging system may further comprise a scanning head coupled to the optical device, the scanning head being arranged to change a position of the optical device relative to the sample material such that the focal region can be scanned across another adjacent area of interest of the sample material.

In accordance with a sixth aspect of the present invention, there is provided an optical fibre coupler for coupling light into a photonic chip, the optical fibre coupler comprising the optical device of the first aspect of the present invention.

In accordance with a seventh aspect of the present invention, there is provided a method of forming an optical device that is arranged to emit electromagnetic radiation, the method comprising:

providing an optical fibre for transmitting electromagnetic radiation between a source of electromagnetic radiation and an area of interest of a sample material; and coupling an optical element comprising a graphene lens to an end portion of the optical fibre in a manner such that, in use, electromagnetic radiation transmitted by the optical fibre through the graphene lens is focused to a focal region within the area of interest of the sample material.

Coupling the optical element to the end portion of the optical fibre may comprise forming the optical element directly or indirectly onto the end portion of the optical fibre.

Forming the optical element onto the end portion of the optical fibre may comprise forming the optical element on a substrate and attaching at least a portion of the substrate with the formed optical element to the end portion of the optical fibre.

The substrate may comprise silicon. Alternatively, the substrate may comprise glass.

Alternatively, the method may further comprise providing the optical element comprising the graphene lens and coupling the optical element to the end portion of the optical fibre may comprise positioning the optical element relative to the end portion of the optical fibre such that the graphene lens covers a core of the optical fibre.

Providing the optical element may comprise forming the optical element on a substrate and chemically (or otherwise) removing the optical element from the substrate.

The optical device may further be arranged to receive electromagnetic radiation that interacted with the area of interest of the sample material.

In this embodiment, the optical element is arranged to receive electromagnetic radiation that interacted with the area of interest of the sample material and the optical fibre is further arranged to transmit the electromagnetic radiation received by the optical element.

BRIEF DESCRIPTION OF THE DRAWINGS

Notwithstanding any other forms which may fall within the scope of the disclosure as set forth in the Summary, specific embodiments will now be described, by way of example only, with reference to the accompanying drawings in which:

FIG. 1(a) depicts a three-dimensional perspective schematic representation of an optical device provided in accordance with an embodiment of the present invention;

FIG. 1(b) depicts a three-dimensional perspective schematic representation of an optical device provided in accordance with a further embodiment of the present invention;

FIG. 2(a) depicts a three-dimensional perspective schematic representation of an optical device provided in accordance with a further embodiment of the present invention;

FIG. 2(b) depicts a three-dimensional perspective schematic representation of an optical device provided in accordance with again a further embodiment of the present invention;

FIG. 16(a) depicts a transmission optical microscopic image of a graphene lens fabricated in accordance with the embodiment of FIGS. 14 and 15;

FIG. 16(b) depicts a topographic profile of the graphene lens of FIG. 16(a);

FIG. 19 is a flow chart of a method of forming an optical device according to an embodiment of the present invention;

FIG. 20 shows two images in a focal plane of a graphene lens forming the optical device in accordance with an embodiment of the present invention;

DETAILED DESCRIPTION OF SPECIFIC EMBODIMENTS

Figure 3:
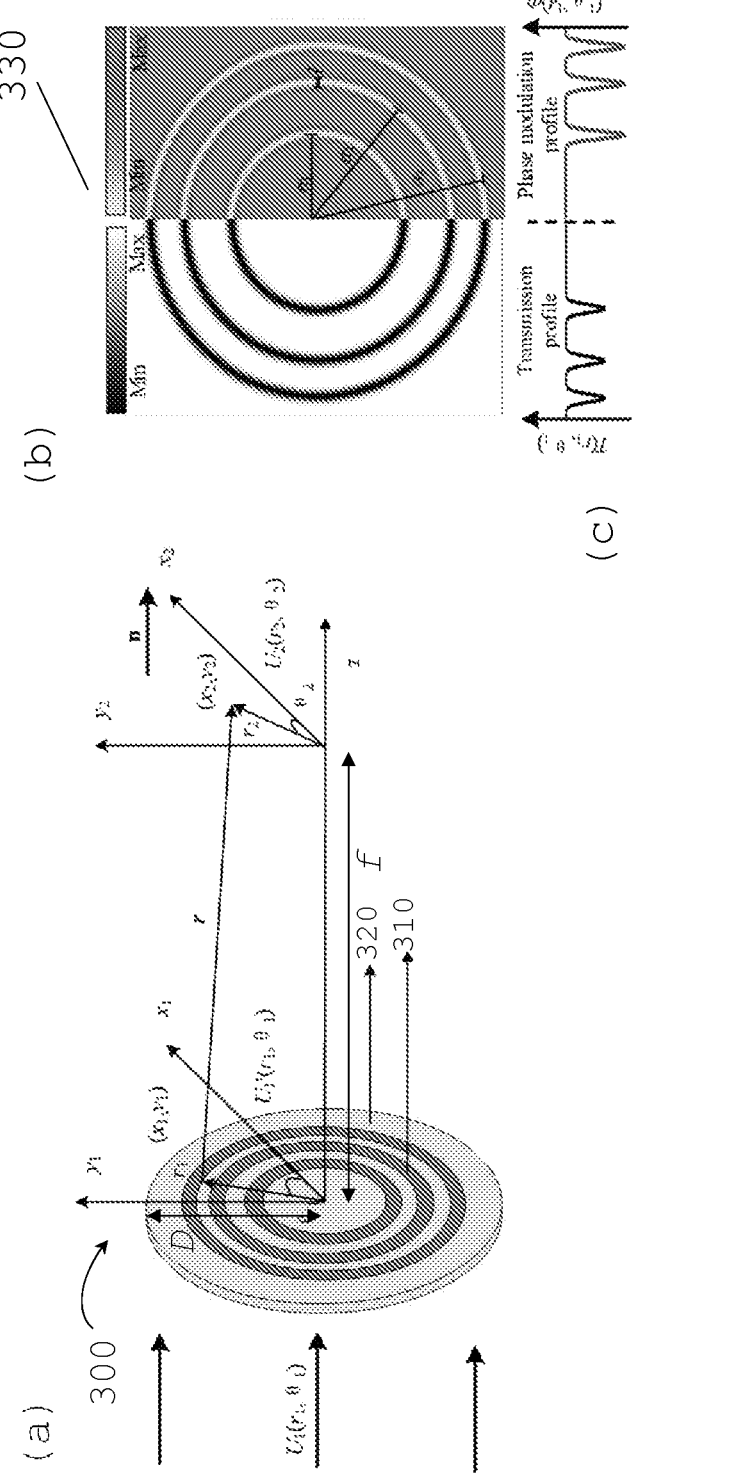
FIG. 3(a) shows a graphene lens provided in accordance with an embodiment of the present invention.
FIG. 3(b) shows a topographic profile of the graphene lens of FIG. 3(a) as measured by an atomic force microscope.
FIG. 3(c) shows transmission and phase modulation profiles provided by the graphene lens of FIG. 3(a)

Embodiments of the present invention relate generally to an optical device that is arranged to emit electromagnetic radiation and which can be used in optical fibre endoscopes or any optical fibre scopes for application in the medical field. For example, suitable applications include those in which examination of the interior of a hollow organ or cavity of a body is to be undertaken, or in which examination of a biological tissue is to be undertaken using optical coherence tomography, for example. The optical device provided in accordance with embodiments of the present invention may also have applications in other fields wherein the optical device is not part of an optical fibre endoscope. For example, the optical device provided in accordance with embodiments of the present invention may have applications in a field for which optical fibre probes having high coupling efficiency are required, such as the field of photonics, wherein the optical device may be used as an ultra-compact fibre coupler to couple light into photonic chips.

However, it will be appreciated that embodiments of the invention are applicable in broader contexts, which will become apparent from the following disclosure.

The optical device provided in accordance with embodiments of the present invention comprises an optical fibre that is arranged to transmit electromagnetic radiation between a source of electromagnetic radiation and an area of interest of a sample material, and an optical element that is coupled to an end portion of the optical fibre and comprises a graphene lens, the graphene lens being arranged to focus electromagnetic radiation transmitted by the optical fibre to a focal region within the area of interest of the sample material.

In accordance with a particular embodiment of the present invention, the optical device is an endoscope and the sample material is a biological tissue.

However, it will be understood that embodiments of the present invention are not limited to biological tissues and that any other suitable sample material may be considered to be within the scope of the present invention.

More specifically, in one embodiment that is illustrated in FIG. 1(*a*), the optical device 100 comprises optical fibre 110 and optical element 120, which is coupled to the end portion or tip of the optical fibre 110. The optical fibre 110 is a single mode optical fibre, or may be a multimode optical fibre, and the optical element 120 comprises a graphene lens 130. The optical fibre 110 comprises an optical fibre core 112 and a cladding 114 and the graphene lens 130 is coupled to the end portion or end tip 116 of the optical fibre core 112. The graphene lens 130 preferably has a diameter that is substantially identical to the diameter of the optical fibre core 112 such that the graphene lens 130 overlaps with the optical fibre core 112. This arrangement of the optical device 100 aims at ensuring an optimal focusing performance of the optical device 100. However, it will be appreciated that, in other embodiments, the diameter of the graphene lens 130 may be smaller than the diameter of the optical fibre core 112, with a slightly lower efficiency as a result.

In the embodiment illustrated in FIG. 1(*b*), the optical device 140 comprises optical fibre 150, which is a multimode optical fibre, and an optical element 160, which is coupled to the end portion or tip 165 of the optical fibre 150 and comprises three graphene lenses 170. The optical fibre 150 more specifically comprises an optical fibre core 152 and a cladding 154 and the graphene lenses 170 are coupled to the end portion of the optical fibre core 152. As illustrated in the inset of FIG. 1(*b*), it will however be understood that the optical element 160 may comprise more than three graphene lenses and may comprise an array of graphene lenses.

In FIG. 2(*a*), there is shown a schematic representation of an optical device 200 provided in accordance with another embodiment of the present invention wherein the optical device 200 comprises a bundle of optical fibres 210, each with an optical element 220 comprising a graphene lens 230 being coupled to corresponding end portions of a respective optical fibre 210 of the bundle. In other words, an end portion of each optical fibre 210 of the bundle is coupled to a respective optical element 220 comprising a graphene lens 230. Similarly to the optical fibres described with reference to FIG. 1, each optical fibre 210 comprises an optical fibre core, e.g. 212, and a cladding, e.g. 214, and on each optical fibre 210, the graphene lens 230 is coupled to the end portion of the optical fibre core 212. The graphene lens 230 preferably has a diameter that is substantially identical to the diameter of the optical fibre core 212 such that the graphene lens 230 overlaps with the optical fibre core 212. This arrangement of the optical device 200 aims at ensuring an optimal focusing performance of the optical device 200.

FIG. 2(*b*) illustrates an optical device 240 provided in accordance with again a further embodiment of the present invention wherein the optical device 240 comprises a bundle of optical fibres 250 and an optical element 260 comprising a graphene lens 270, the optical element being coupled to an end portion 280 of the bundle 250, i.e. the optical element is coupled to each optical fibre 250 of the bundle.

The optical elements 120, 160, 220, 260 comprising the respective graphene lenses 130, 170, 230, 270 may be formed directly or indirectly on the respective end-portions of the optical fibres.

Alternatively, the optical elements may be attached to the end-portion of the respective optical fibres by one or more attachment means such as an adhesive layer or retaining device.

With reference to FIGS. 3 to 18, there will now be discussed methods of forming or fabricating the graphene lens of the optical device provided in accordance with embodiments of the present invention.

As illustrated in FIG. 3(a), the graphene lens 300 provided in accordance with embodiments of the present invention comprises concentric rings, which include opaque zones 310 corresponding to graphene zones 310, and transparent zones 320 also referred to as air zones. The graphene lens 300 has a diameter 'D' and a focal length 'f'. The graphene lens plane corresponds to a diffraction plane $r_1-\theta_1$, $r_1$ and $\theta_1$ being the polar coordinates in the graphene lens plane wherein $$r_1 = \sqrt{x_1^2 + y_1^2}.$$

he $r_2-\theta_2$ plane is the observation plane, $r_2$ and $\theta_2$ are the polar coordinates in the observation plane wherein $$r_2 = \sqrt{x_2^2 + y_2^2}.$$

Z is the distance between the diffraction plane and the observation plane, and the observation plane is usually the focal plane whereby z=f. An incident light wave characterized by the electric field (E-field) $U_1(r_1,\theta_1)$ is propagating along the z axis in the positive z direction. The amplitude and phase of the incident light are both modulated simultaneously by the graphene lens and the light wave immediately behind the graphene lens is characterised by the E-field $U'_1(r_1,\theta_1)$.

The electric field modes of an optical fibre are key parameters for the design of an on-fibre tip graphene based lens. The graphene lens was designed according to the Rayleigh-Sommerfeld (RS) diffraction theory for which the E-field at an arbitrary observation plane at a distance z can be written as:

$$U_2(r_2, \theta_2, z) = \frac{1}{2\pi}$$
$$\int_0^{2\pi} \int_0^{\infty} U'_1(r_1, \theta_1) \left( -ik - \frac{1}{\sqrt{z^2 + r_1^2 + r_2^2 - 2r_1 r_2 \cos(\theta_1 - \theta_2)}} \right) *$$
$$\frac{\exp\left(-ik\sqrt{z^2 + r_1^2 + r_2^2 - 2r_1 r_2 \cos(\theta_1 - \theta_2)}\right)}{z^2 + r_1^2 + r_2^2 - 2r_1 r_2 \cos(\theta_1 - \theta_2)} z r_1 dr_1 d\theta_1$$
(1)

where $k=2\pi/\lambda$ is the wave vector, $\lambda$ is the wavelength of the incident beam in vacuum. When the incident wave $U_1(r_1,\theta_1)$ impinges on the graphene lens, the beam is partly absorbed and diffracted by the graphene zones 310 and air zones 320. $U_1'(r_1, \theta_1)$ can be expressed as:

$$U'_1(r_1, \theta_1) = U_1(r_1, \theta_1) * t(r_1, \theta_1) * e^{-ik(\Phi(r_1,\theta_1))}$$
(2)

where $t(r_1,\theta_1)$ is the transmission coefficient, $\phi(r_1,\theta_1)$ is the phase modulation, as shown in FIG. 3(c).

The E-field distribution in the focal region of the graphene lens can be calculated using the RS diffraction theory:

$$U_2(r_2, \theta_2, z) = -\frac{i}{\lambda} \int \int U'_1(r_1, \theta_1) \frac{\exp(ikr)}{r} \cos(n, r) \, dr_1 d\theta_1$$
(3)

where $r =$ $$\sqrt{z^2 + (x_2 - x_1)^2 + (y_2 - y_1)^2} = \sqrt{z^2 + r_1^2 + r_2^2 - 2r_1 r_2 \cos(\theta_1 - \theta_2)},$$

n denotes the unit vector normal toward the observation plane, r is the unit vector of r direction from $r_1$ to $r_2$ as shown in FIG. 1(a). The field distribution in the focal region in cylindrical coordinate system can thus be determined using the following equation:

$$U_2(r_2, \theta_2, z) = -\frac{i}{\lambda} \int_0^{2\pi} \int_0^{\infty} U'_1(r_1, \theta_1)$$
$$\frac{\exp\left(-ik\sqrt{z^2 + r_1^2 + r_2^2 - 2r_1 r_2 \cos(\theta_1 - \theta_2)}\right)}{z^2 + r_1^2 + r_2^2 - 2r_1 r_2 \cos(\theta_1 - \theta_2)} z r_1 dr_1 d\theta_1$$
(4)

To design the Graphene lens with the targeted focal length f and diameter D based on the RS diffraction theory, the intensity distribution on the z axis is considered, namely with $r_2=0$, $\theta_2=0$, and z=f. Therefore, the field distribution along z axis is:

$$U_2(f) = -\frac{i}{\lambda} \int_0^{2\pi} \int_0^{\infty} U'_1(r_1, \theta_1) \frac{\exp\left(-ik\sqrt{f^2 + r_1^2}\right)}{f^2 + r_1^2} z r_1 dr_1 d\theta_1 =$$
$$-\frac{i2\pi}{\lambda} \int_0^{\infty} U'_1(r_1) \frac{\exp\left(-ik\sqrt{f^2 + r_1^2}\right)}{f^2 + r_1^2} f r_1 dr_1$$
(5)

For the targeted focal length f, $U_2(f)$ is decided by $r_1$ only. Based on the Euler's equation, the field distribution along z axis can be rewritten as:

$$U_2(r_1) = \frac{-2\pi z}{\lambda} \left( i \int_0^{\infty} U_1(r_1) \frac{\cos\left(-k\sqrt{z^2 + r_1^2}\right)}{z^2 + r_1^2} r_1 dr_1 - \int_0^{\infty} U_1(r_1) \frac{\sin\left(-k\sqrt{z^2 + r_1^2}\right)}{z^2 + r_1^2} r_1 dr_1 \right)$$
(6)

Therefore, the intensity distribution on the z axis can be simplified to:

$$I(r_1) = abs([(r_1)]^2 = \left(\frac{2\pi f}{\lambda}\right)^2 \left[ \left( \int_0^{\infty} U_1(r_1) \frac{\cos\left(-\sqrt{f^2 + r_1^2}\right)}{f^2 + r_1^2} r_1 dr_1 \right)^2 + \left( \int_0^{\infty} U_1(r_1) \frac{\sin\left(-k\sqrt{f^2 + r_1^2}\right)}{f^2 + r_1^2} r_1 dr_1 \right)^2 \right]$$
(7)

The mode field $U_1(r_1)$ of a single mode fibre can be approximated to a Gaussian distribution wherein:

$$U_1(r_1) = \sqrt{\frac{2}{\pi\omega_1^2(z)}} \exp\left(-\frac{r_1^2}{\omega_1^2(z)}\right) \tag{8}$$

$$\text{where } \omega_1(z) = \omega_0\sqrt{1 + \frac{z\lambda}{\pi\omega_0^2}} \tag{9}$$

where $\omega_1(z)$ is the radius of a Gaussian beam, and $\omega_0$ is the radius of the Gaussian beam waist.

To simplify the analyzation, the change of $\omega_1(z)$ is disregarded due to the real situation that z is very small, so $\omega_1(z) \approx \omega_0$, same as the radius of the fibre core. The Gaussian beam is considered to have no divergence angle. Then in equation (8), when z is fixed and the intensity $I(r_1)$ is calculated as per equation 7 (i.e. with $r_2=0$ and $\theta_2=0$), the phases $\phi(r_1,\theta_1)$ are only effected by the factor of $$\exp\left(-\frac{i|k|r_1^2}{2z}\right),$$

which is in relationship with $r_1$.

To find out the minimal points on the intensity distribution $I(r_1)$, taking the derivative of equation 7, the contribution of $I(r_1)$ on point f along $r_1$ can be obtained using the following equation:

$$\frac{dI}{dr_2} = \tag{10}$$

$$2*\left(\frac{2\pi f}{\lambda}\right)^2\left[\left(\frac{\cos\left(-k\sqrt{f^2+r_1^2}\right)}{f^2+r_1^2}r_1\int_0^\infty \frac{\cos\left(-k\sqrt{f^2+r_1^2}\right)}{f^2+r_1^2}r_1 dr_1\right) + \right.$$

$$\left.\left(\frac{\sin\left(-k\sqrt{f^2+r_1^2}\right)}{f^2+r_1^2}r_1\int_0^\infty \frac{\sin\left(-k\sqrt{f^2+r_1^2}\right)}{f^2+r_1^2}r_1 dr_1\right)\right]$$

where, $$\int_0^\infty \frac{\cos\left(-k\sqrt{f^2+r_1^2}\right)}{f^2+r_1^2}r_1 dr_1 = \tag{11}$$

$$\int_0^\infty \frac{\cos\left(-k\sqrt{f^2+r_1^2}\right)}{f^2+r_1^2}\frac{1}{2}d(r_1^2+f^2) =$$

$$\int_0^\infty \frac{1}{2}\frac{\cos(-kR)}{R^2}dR^2 = \int_0^\infty \frac{\cos(-kR)}{R}dR$$

where $R = \sqrt{f^2+r_1^2}$.

As we know:

$$\cos R = 1 - \frac{R^2}{2!} + \frac{R^4}{4!} + (-1)^n\frac{R^{2n}}{(2n)!} \tag{12}$$

$$\sin R = R - \frac{R^3}{3!} + \frac{R^5}{5!} + (-1)^n\frac{R^{2n+1}}{(2n+1)!} \tag{13}$$

where n is an integer greater than, or equal to, 0. There is no analytic expression of equations 12 and 13 and consequently no analytic expression of indefinite integral equation 11. As such, a numerical simulation software package such as MATLAB can be used to determine the minimal points using equation 7.

Using numerical simulation, the minimal points on the intensity distribution $I(r_1)$ predict the ring radii of the graphene lens with a focal length f. In particular, the extreme points of the intensity distribution $I(r_1)$ indicate the ring positions that contribute constructive interference to the intensity. In the meantime, the diameter can be decided by the number of rings. In this way, graphene lenses can be designed according to different incident fields $(U_1(r_1,\theta_1))$.

FIG. 3(b) illustrates an exemplary topographic profile 330 of the graphene lens 300 as measured by an atomic force microscope. In the present specific embodiment, the graphene lens 300 comprises three concentric rings composed of graphene, each having a thickness I and a respective radius $a_1$, $a_2$, $a_3$. Examples of values for the three radii $a_1$, $a_2$, $a_3$ for four different graphene lenses designed and fabricated in accordance with embodiments of the present invention are illustrated in Table 1 below.

TABLE 1

| Radius | Lens1 (μm) | Lens2 (μm) | Lens3 (μm) | Lens4 (μm) |
|---|---|---|---|---|
| $a_1$ | 1.543 | 3.135 | 1.27 | 1.42 |
| $a_2$ | 2.665 | 4.670 | 2.15 | 2.31 |
| $a_3$ | 3.559 | 5.903 | 3.01 | 3.08 |

Figure 4:
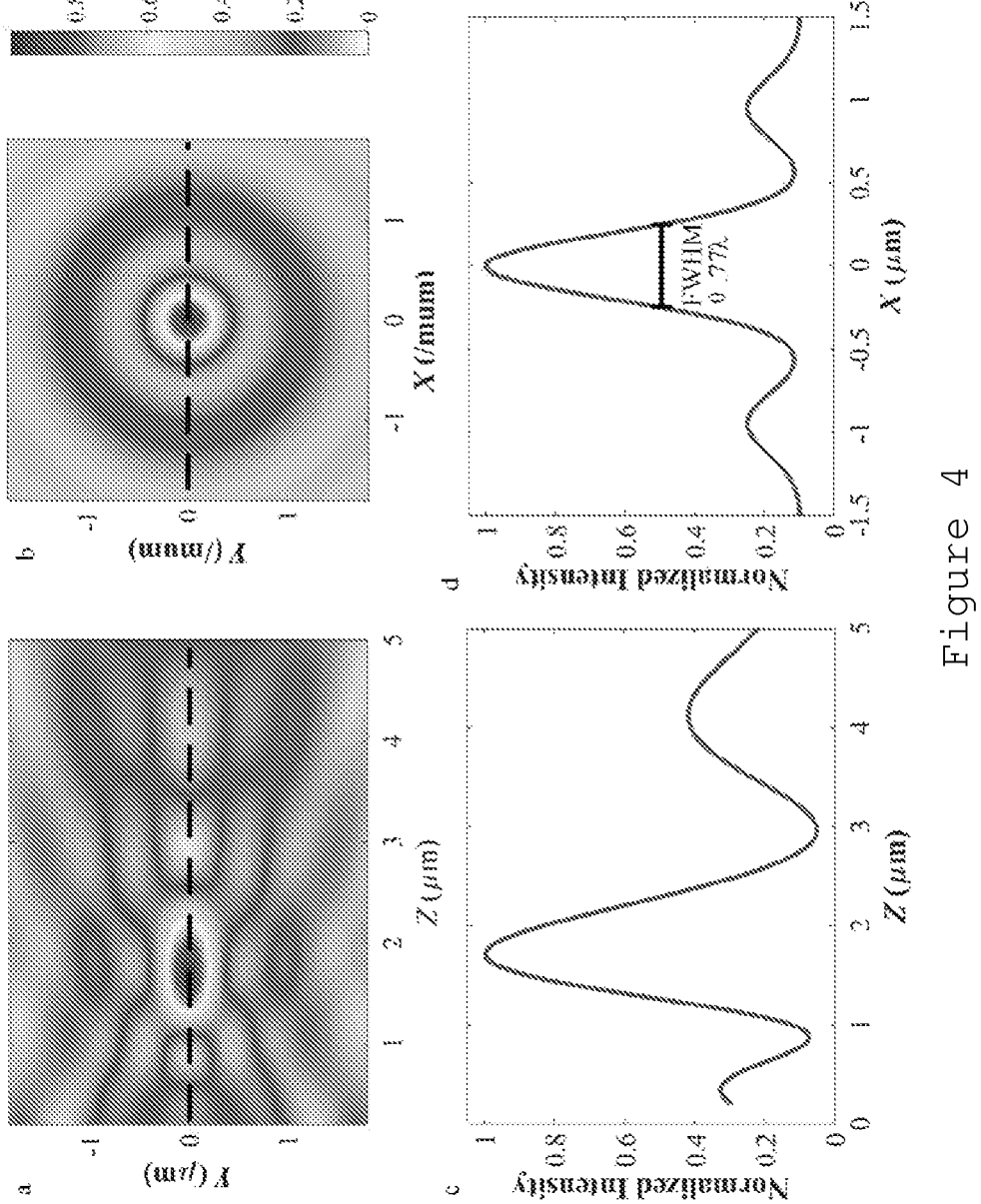
FIGS. 4(a) and 4(b) illustrate theoretical intensity distributions in an axial plane and lateral plane respectively for a graphene lens design according to one embodiment.
FIGS. 4(c) and 4(d) illustrate intensity distributions along the black dash lines of FIGS. 4(a) and 4(b) respectively.

The parameters of Lens3 are based on a fibre with a 6 μm diameter core. The theoretical results of simulating Lens3 are shown in FIG. 4, in which the incident wavelength is 0.633 μm. FIGS. 4(a) and 4(b) show the axial and lateral plane of the focal spot. FIGS. 4(c) and 4(d) show the profile along the black dash lines in FIGS. 4(a) and 4(b) respectively. The focal length is 1.71 μm as shown in FIG. 4(c), the FWHM along the x-axis is 0.49 μm (0.77λ).

Figure 5:
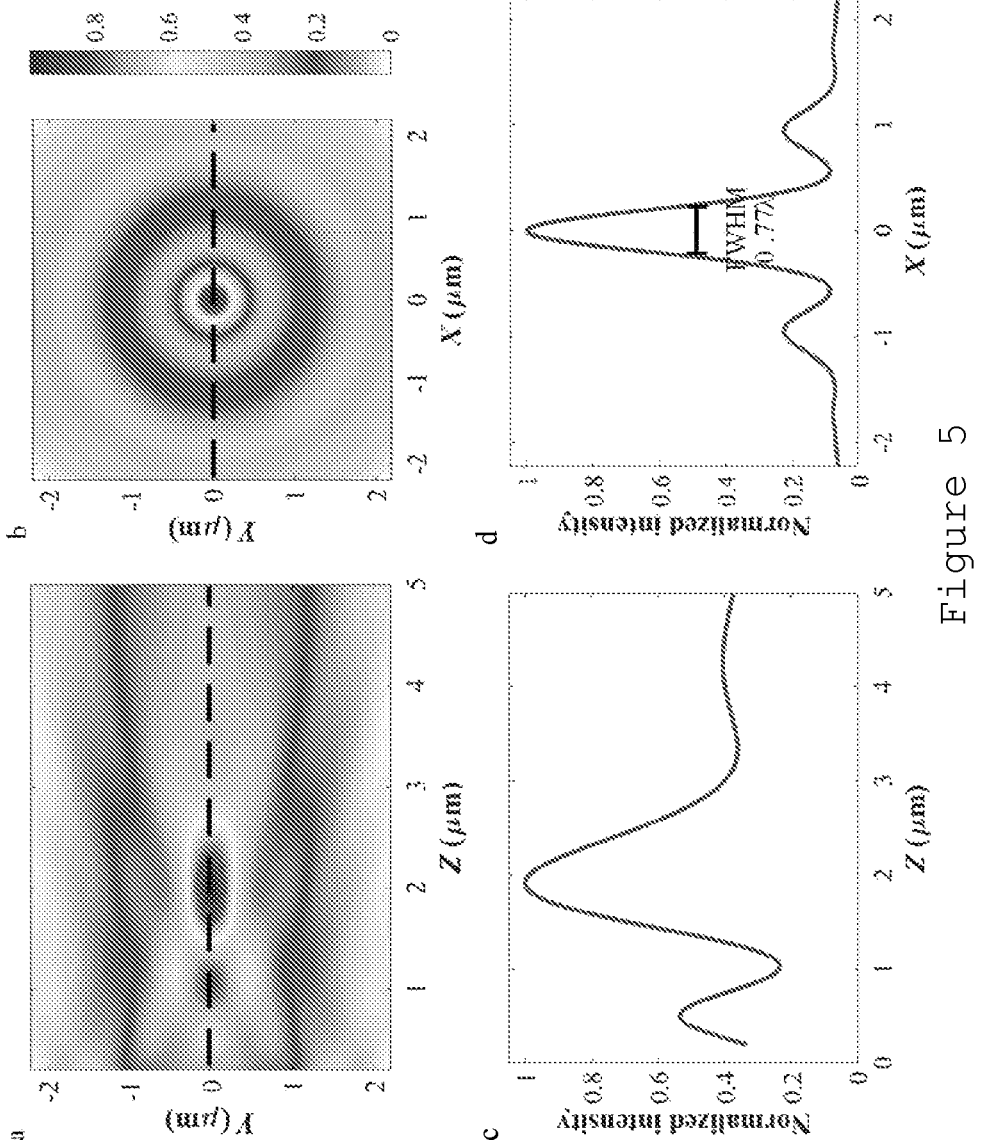
FIGS. 5(a) and 5(b) illustrate theoretical intensity distributions in an axial plane and lateral plane respectively for a graphene lens design according to another embodiment.
FIGS. 5(c) and 5(d) illustrate intensity distributions along the black dash lines of FIGS. 5(a) and 5(b) respectively.

The parameters of Lens4 in Table 1 are based on a single mode fibre for 0.633 μm wavelength (e.g. 630HP model from Thorlabs). The intensity distributions of Lens4 are illustrated in FIG. 5. FIGS. 5(a) and 5(b) show the axial and lateral plane of the focal spot, while FIGS. 5(c) and 5(d) show the profile along the black dash lines in FIGS. 5(a) and 5(b). Here the focal length is 1.91 μm as shown in FIG. 5(c), the FWHM along the x-axis is 0.49 μm (0.77λ), as shown in FIG. 5(d).

However, it will be understood that embodiments of the present invention are not limited to a graphene lens having three graphene concentric rings and that formation of graphene lenses comprising more than or less than three graphene concentric rings is also considered to be within the scope of the present invention.

The inventors have also designed higher order graphene lenses with long focal lengths and greater numbers of concentric rings. Some of these designs include lenses with dozens of concentric rings. Examples of the first ten ring radii are listed in Table 2 below.

TABLE 2

| Radius | Lens5 (μm) | Lens6 (μm) |
|---|---|---|
| $a_1$ | 6.81 | 9.62 |
| $a_2$ | 10.56 | 14.88 |
| $a_3$ | 13.58 | 18.72 |
| $a_4$ | 17.59 | 21.91 |
| $a_5$ | 19.42 | 24.70 |
| $a_6$ | 21.10 | 27.22 |

TABLE 2-continued

| Radius | Lens5 (µm) | Lens6 (µm) |
|--------|------------|------------|
| $a_7$ | 22.68 | 29.54 |
| $a_8$ | 24.18 | 31.70 |
| $a_9$ | 25.60 | 33.74 |
| $a_{10}$ | 26.96 | 35.67 |

Figure 6:
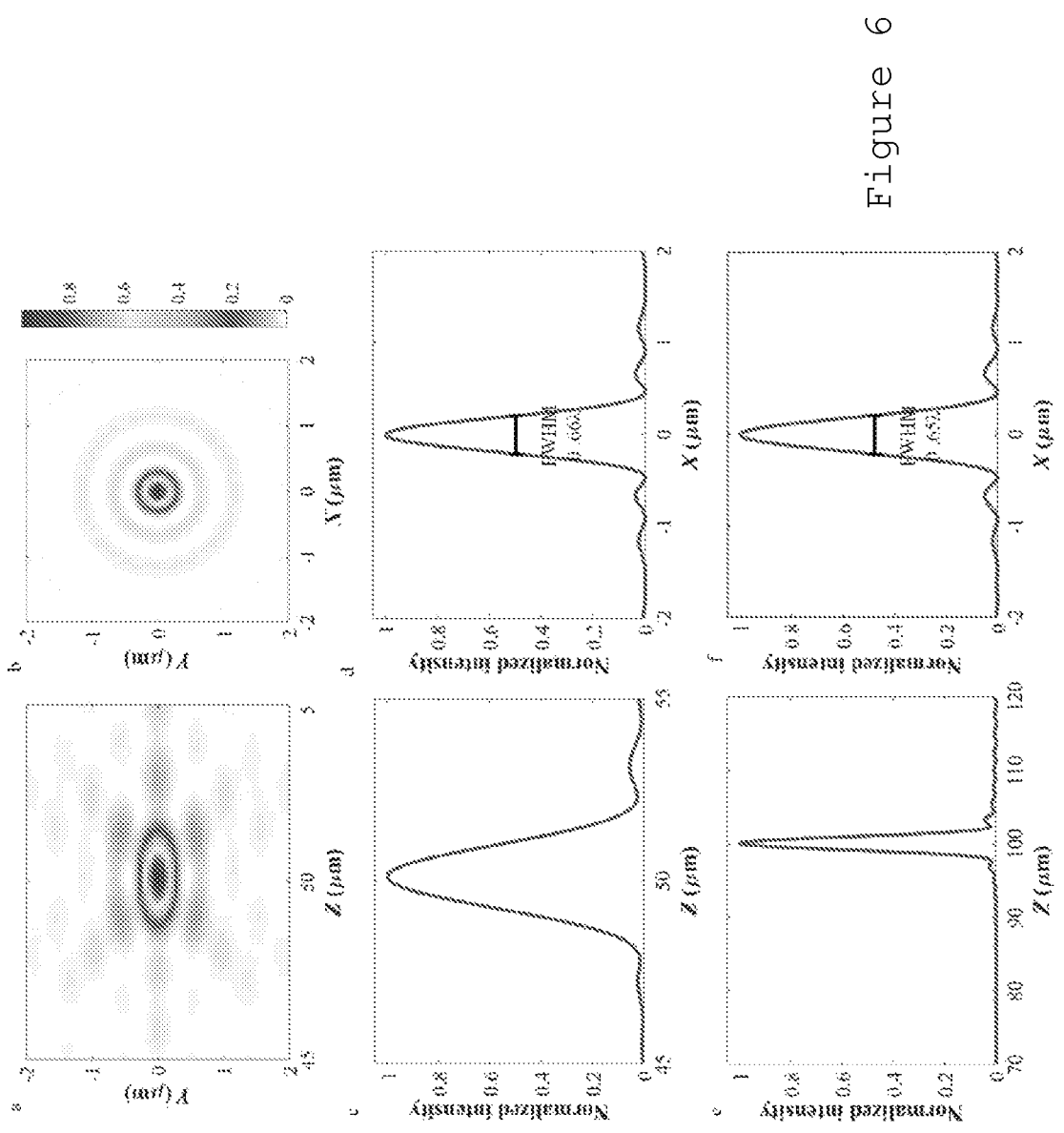
FIGS. 6(a) and 6(b) illustrate theoretical intensity distributions in an axial plane and lateral plane respectively for a graphene lens design according to a further embodiment.
FIGS. 6(c) and 6(d) illustrate intensity distributions along the black dash lines of FIGS. 6(a) and 6(b) respectively.
FIGS. 6(e) and 6(f) illustrated theoretical intensity distribution profiles along a line in the axial plane and the lateral plane for a graphene lens design according to a still further embodiment.

The Intensity distributions corresponding to Lens5 in Table 1 are shown in FIG. 6. FIG. 6(a) and FIG. 6(b) show the axial and lateral plane of the focal spot respectively. FIG. 6(c) and FIG. 6(d) show the profiles along the black dash lines in FIG. 6(a) and FIG. 6(b) respectively. The focal length of this lens is 50 µm as shown in FIG. 6(c), while the FWHM along the x-axis is 0.42 µm (0.66λ), as shown in FIG. 6(d).

FIG. 6(e) and FIG. 6(f) illustrate the profiles along the axial and lateral planes for Lens6 in Table 2. As shown in FIG. 6(e), the focal length of this lens is 100 µm, and the FWHM along the x-axis is 0.41 µm (0.65 A), as shown in FIG. 6(d). It was found that with an increase in focal length, the FWHM remains small, which means, in theory, on-fibre tip graphene lenses with long focal lengths maintain their high resolution.

Figure 7:
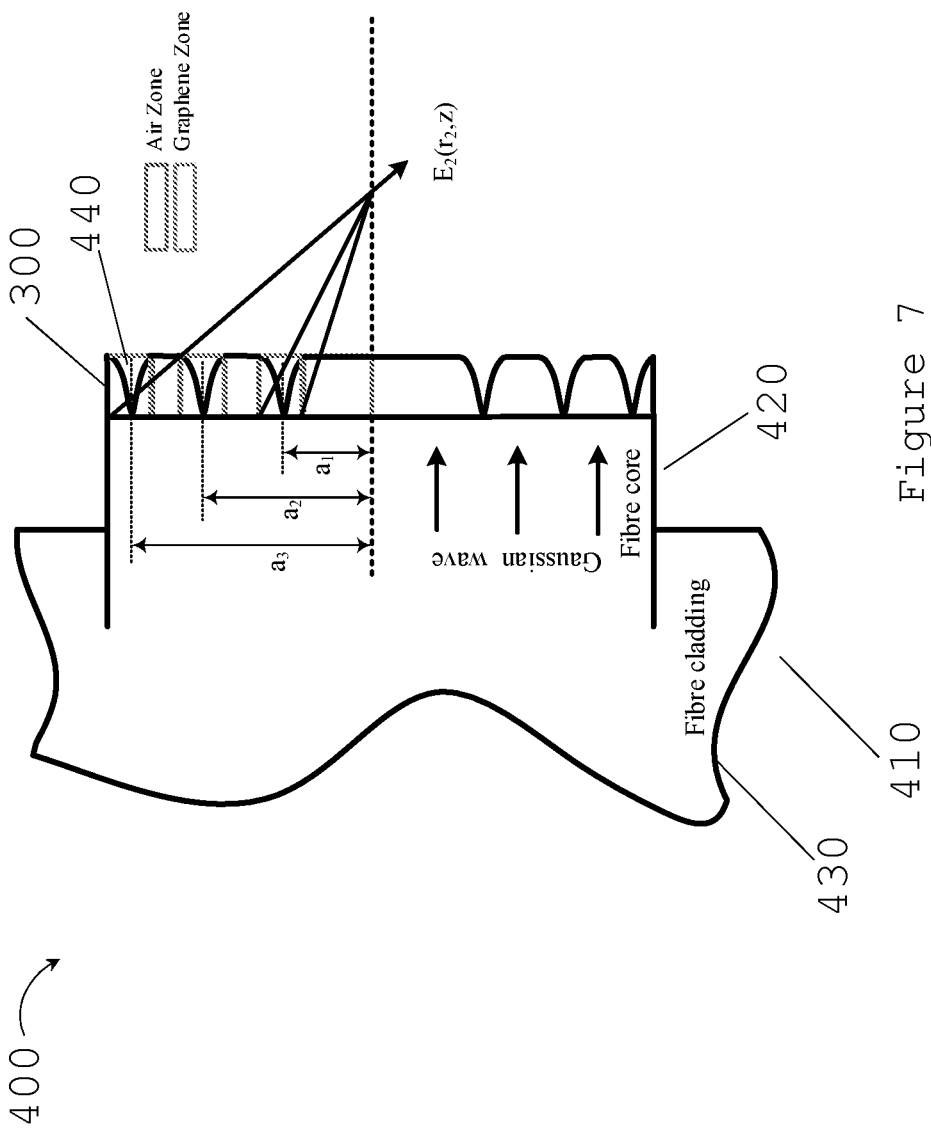
FIG. 7 shows a schematic representation of an optical device in accordance with an embodiment of the present invention.

Further, FIG. 3(c) shows a transmission profile $t(r_1, \theta_1)$ and phase modulation profile $\phi(r_1, \theta_1)$ of the light modulated by the graphene lens 300. FIG. 7 illustrates a schematic representation 400 of an optical device comprising an optical fibre 410 having an optical fibre core 420 and a cladding 430, and an optical element with graphene lens 300 coupled to the end portion or end tip of the optical fibre 410. The three concentric rings having respective radii $a_1$, $a_2$, $a_3$ are schematically represented as well as the Gaussian wave distribution 440 of the light incident on the graphene lens 300.

Figure 8:
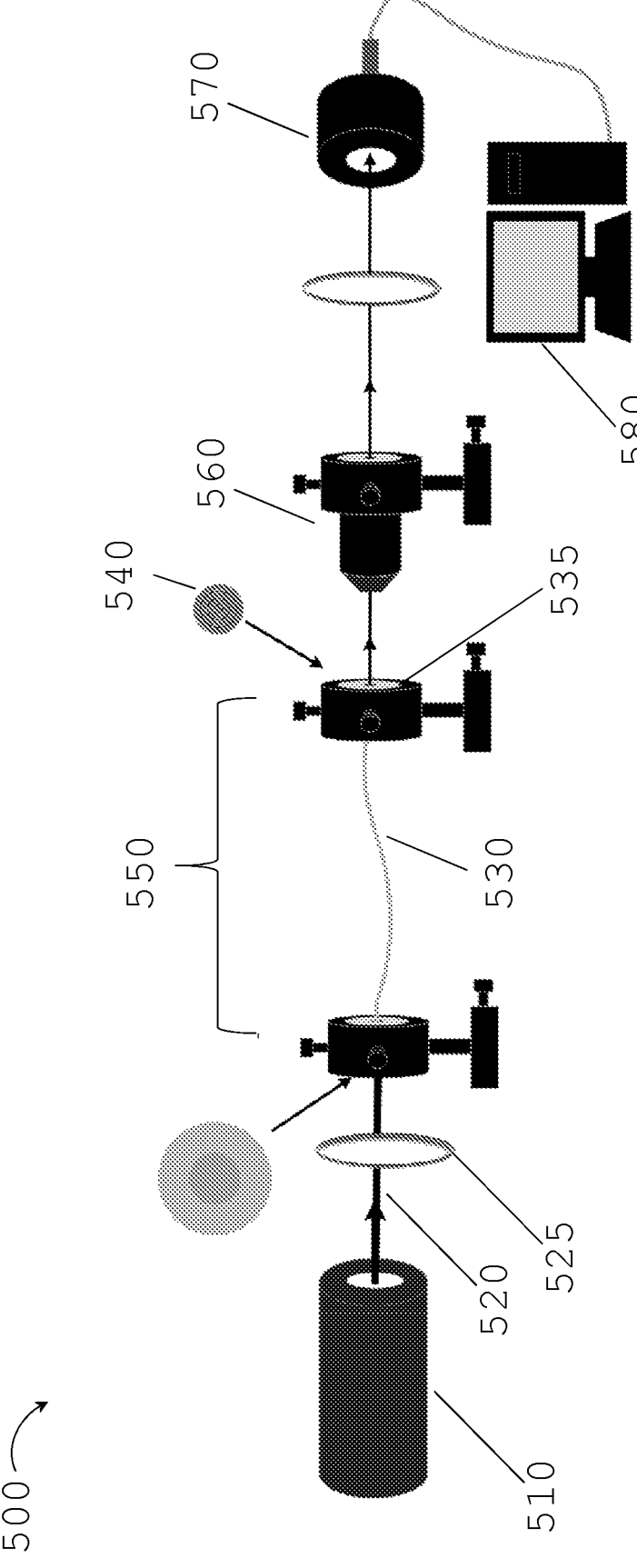
FIG. 8 shows an experimental set-up for an optical test system in accordance with an embodiment of the present invention.
Figure 9:
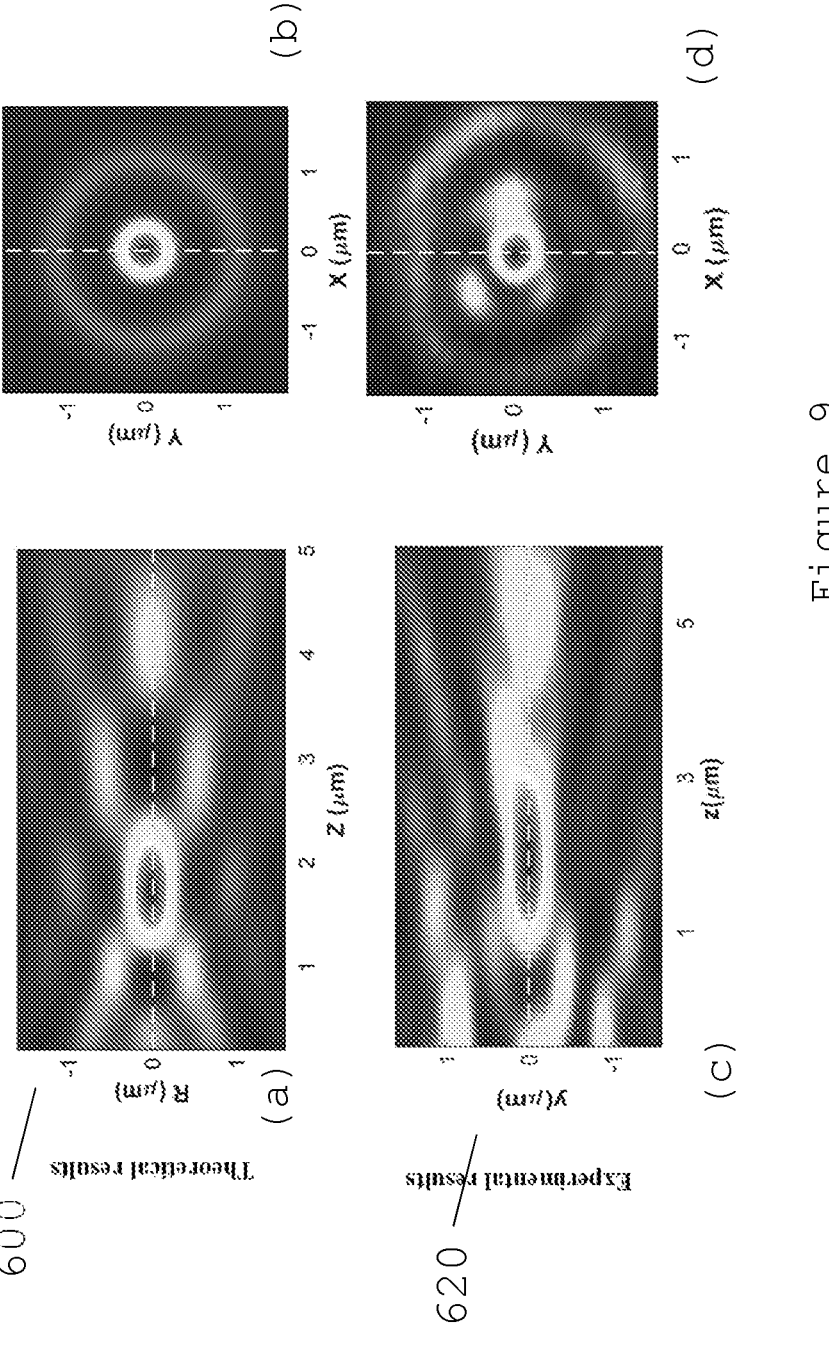
FIGS. 9(a) and 9(b) illustrate theoretical focal intensity distributions (a) in the x-y plane and (b) in the x-z plane for an optical device provided in accordance with an embodiment of the present invention.
FIGS. 9(c) and 9(d) illustrate experimental focal intensity distributions (a) in the x-y plane and (b) in the x-z plane for the optical device provided in accordance with the embodiment of FIGS. 9(a) and 9(b)
Figure 10:
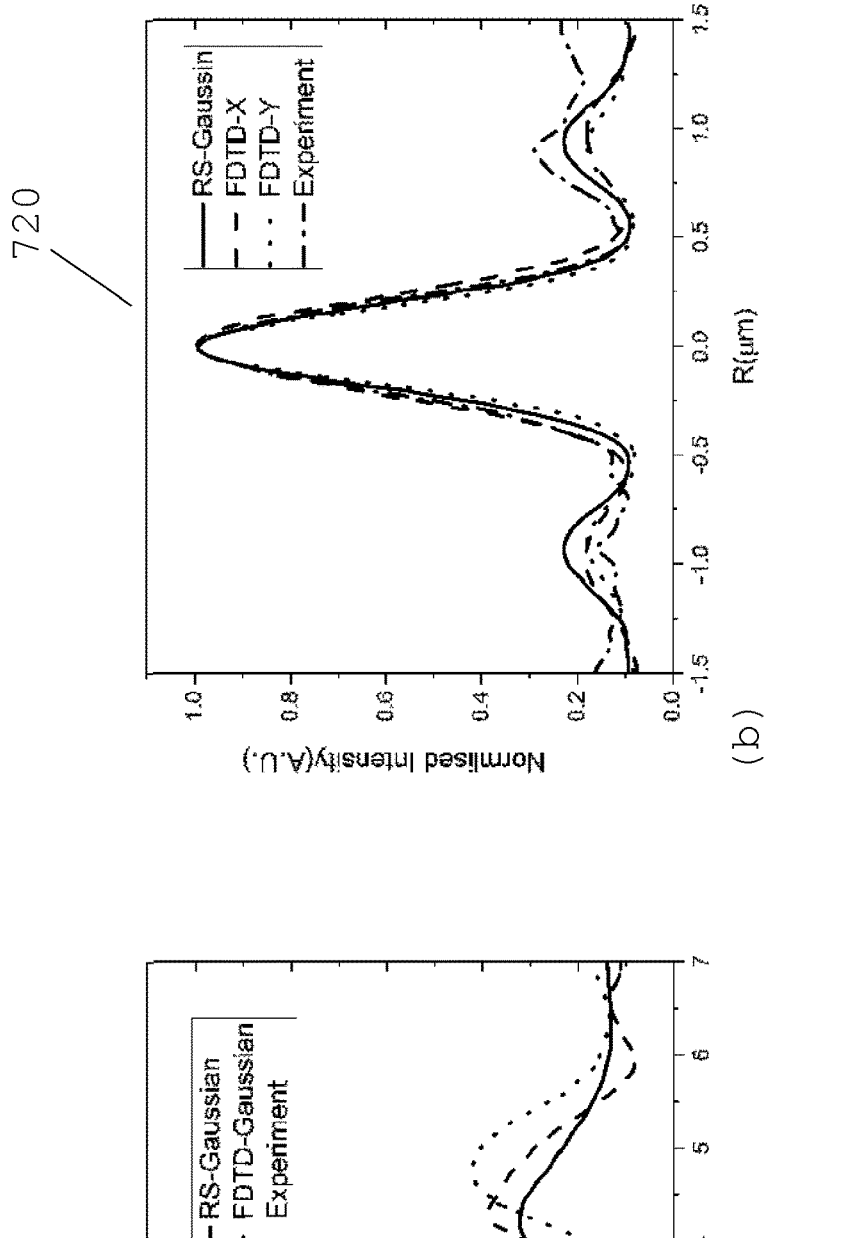
FIGS. 10(a) and 10(b) show theoretical and experimental plots of focal intensity distributions measured for an optical device provided in accordance with an embodiment of the present invention.

The focusing performance of the optical device, such as optical device 100, 140, 200 or 240, comprising a graphene lens having the design and structure of graphene lens 300, is tested using an experimental set-up, such as optical test system 500 illustrated schematically in FIG. 8. A source of electromagnetic radiation 510 (e.g. laser) is provided that emits a laser beam 520. The laser beam 520 is focused by a lens 525 onto the flat tip side of an optical fibre 530 and transmitted by the optical fibre 530 to the optical element 535 comprising the graphene lens 540 positioned and coupled to the end portion of optical fibre 530. The optical fibre 530 coupled to the optical element comprising the graphene lens 540 thus form an optical device 550. An objective 560 (in this particular embodiment, an 80x objective) is used to scan the focusing region or spot of the graphene lens 540 and the focal intensity distribution of the graphene lens 540 is collected by a CCD camera 570. The focal intensity distribution of the graphene lens 540 can then further be observed using a graphical user interface 580.

FIGS. 9(a) and 9(b) illustrate theoretical focal intensity distributions 600 expected to be obtained for the optical device 550 in the z-y plane and x-y plane, respectively. FIGS. 9(c) and 9(d) show the actual focal intensity distribution obtained using the experimental set-up 500 for the optical device 550 in the z-y focal plane and x-y focal plane, respectively.

Further, FIGS. 10(a) and 10(b) show plots 700 and 720 of focal intensity distributions along the optical z axis and along the radial r axis, respectively, measured for the optical device 550. In particular, on both plots 700 and 720, the black curves show theoretical results obtained using different theoretical methods while the light grey curves show experimental results obtained for an optical device such as optical device 550 comprising the graphene lens 540 having a design such as design illustrated in FIG. 3.

It can be seen from plots 700 and 720 that a sub-micron optical resolution was achieved by the optical device 550 comprising the graphene lens 540. In comparison to other types of optical lenses such as the GRIN lens, which is typically used in single mode optical fibres for use in endoscopes and OCT imaging and commonly provides an optical resolution of ~10 µm for axial direction and ~30 µm for transverse direction. (see, e.g., Ji, Chong-ke, et al. "Micrometer-resolution in-fiber OCT probe with tunable working distance." Optics Express 24.17 (2016): 19814-19823), it can be said that the graphene lens provided in accordance with embodiments of the present invention allows achieving a substantially improved optical resolution.

The fabrication of a graphene lens provided in accordance with the embodiment illustrated in FIG. 3, for an optical device, such as optical devices 100, 140, 200 or 240, can be divided into three steps:

i) Fabricate a graphene oxide (GO) film;
    ii) Convert the GO film into a reduced graphene oxide (RGO) film; and
    iii) Laser ablate the RGO film to create the graphene lens.

These three steps will now be described in more detail with reference to FIGS. 11 to 16.

i) Fabrication of the GO Film

The inventors have used two alternative methods to fabricate the GO film, namely a vacuum filtration method and a self-assemble method.

However, it will be understood that other methods may be used, such as a drop casting method and a spray coating method.

Vacuum Filtration Method

Figure 11:
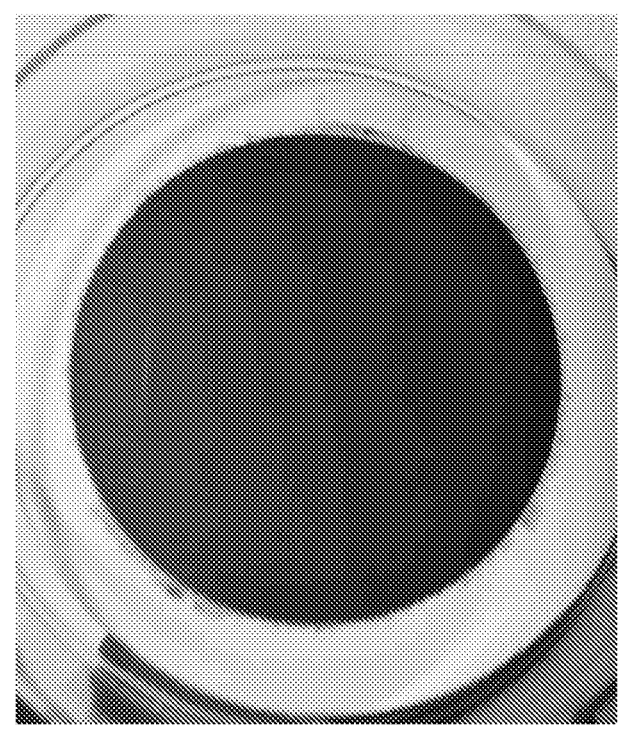
FIG. 11 illustrates the formation of a graphene oxide film in accordance with an embodiment of the present invention.

A solution of GO is drawn through a filter and an evenly deposited film is formed by leaving the solution drip away. The diameter of the filter is in the range from 1 mm to ~90 mm. The concentration of the GO solution can be in the range of 0.01 mg/ml to 1 mg/ml. Lower concentrations will help disperse GO flakes better and thus improve the uniformity of the film. The thickness of the GO film is controlled by the mass of the GO flakes in the solution and accordingly can be in the range from 10 nm up to 10 µm. The solvent in this embodiment is water. One example of a filtrated GO film 800 is shown in FIG. 11. In this example, a solution comprising 3 mg of GO flakes was used and the thickness of the GO film so formed was about 1.5 µm. The GO film can then be transferred to a cover glass substrate for a lens application. FIGS. 12(a)-(d) show GO films fabricated by the vacuum filtration method, having different thicknesses and being deposited on a cover glass substrate. The GO films on cover glass substrate illustrated in FIGS. 12(a)-(d) have the following respective thicknesses: 40 nm (FIG. 12(a)), 70 nm (FIG. 12(b)), 160 nm (FIG. 12(c)), and 200 nm (FIG. 12(d)).

Figure 12:
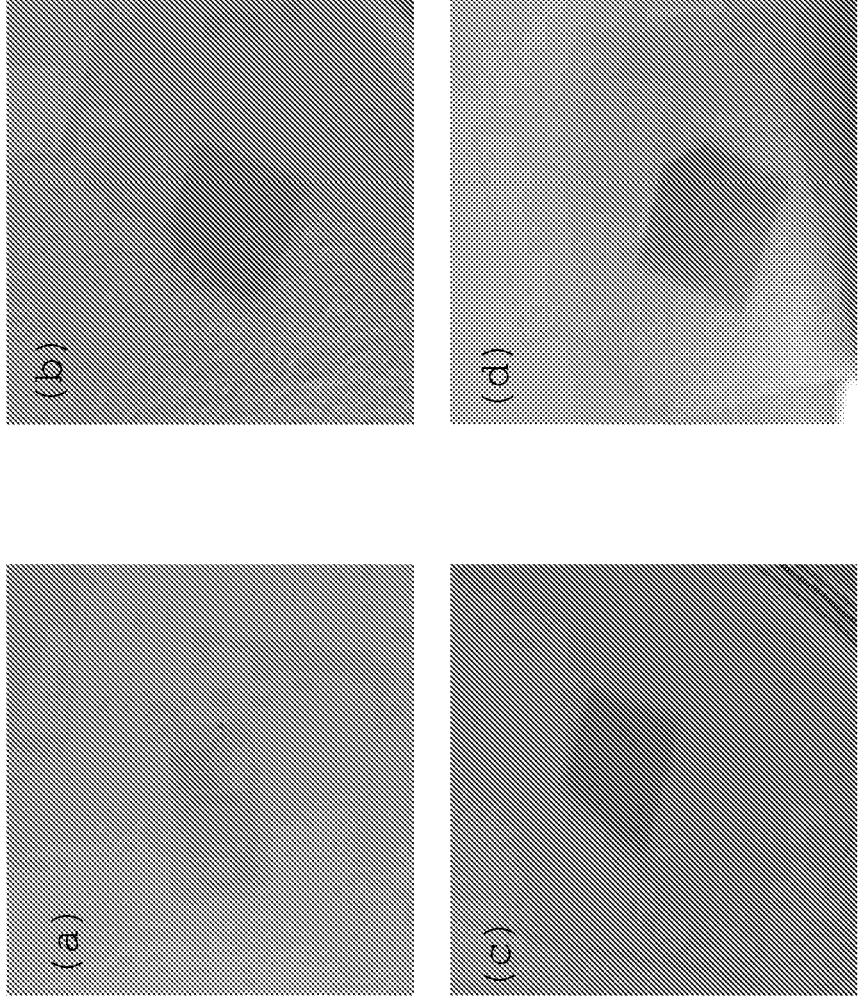
FIGS. 12(a)-(d) illustrate graphene oxide films having respective different thicknesses and formed on a substrate in accordance with an embodiment of the present invention.
Figure 13:
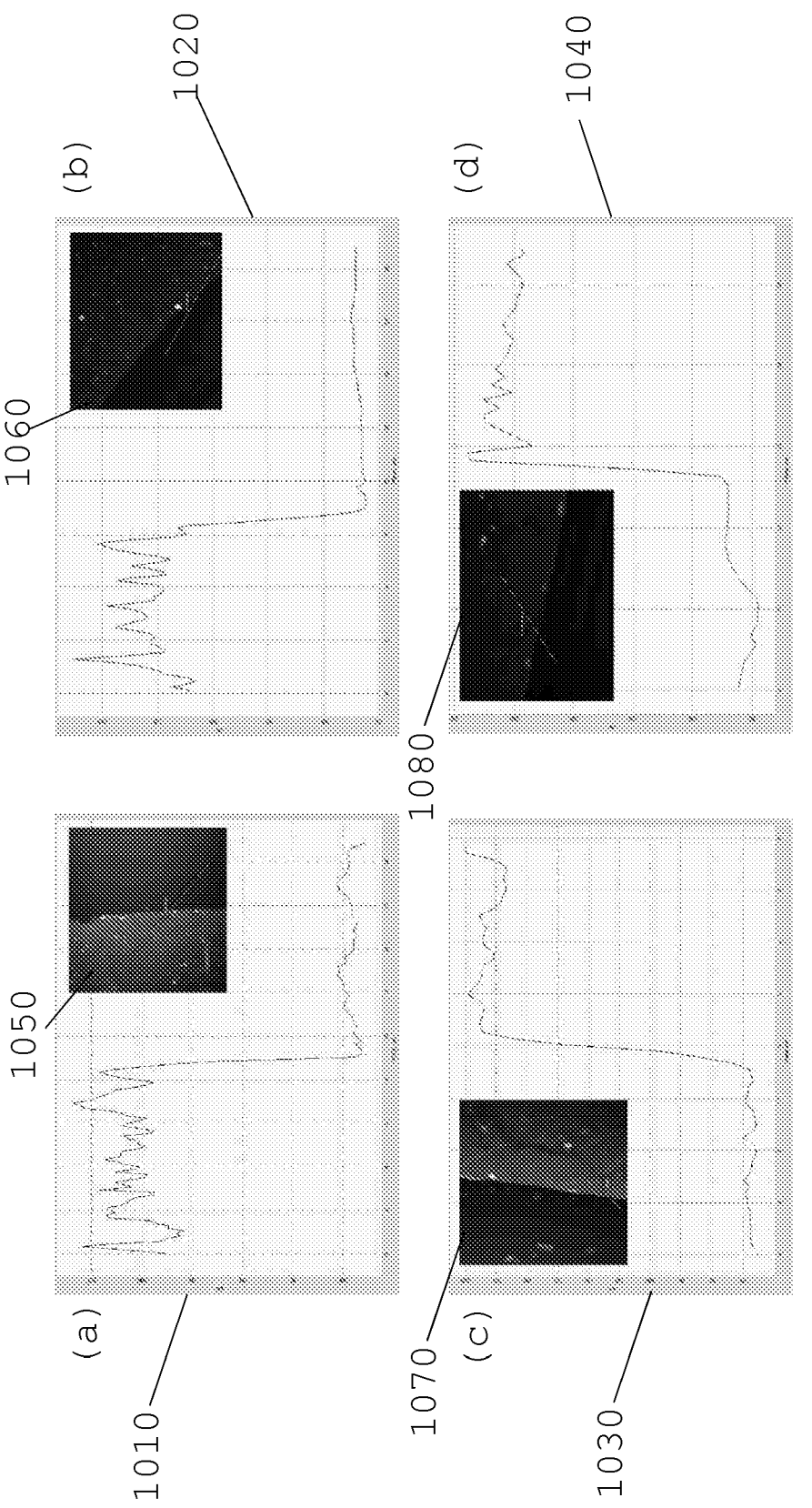
FIGS. 13(a)-(d) show respective graphs and atomic force microscope images of the graphene oxide films of FIGS. 12(a)-(d)
Figure 14:
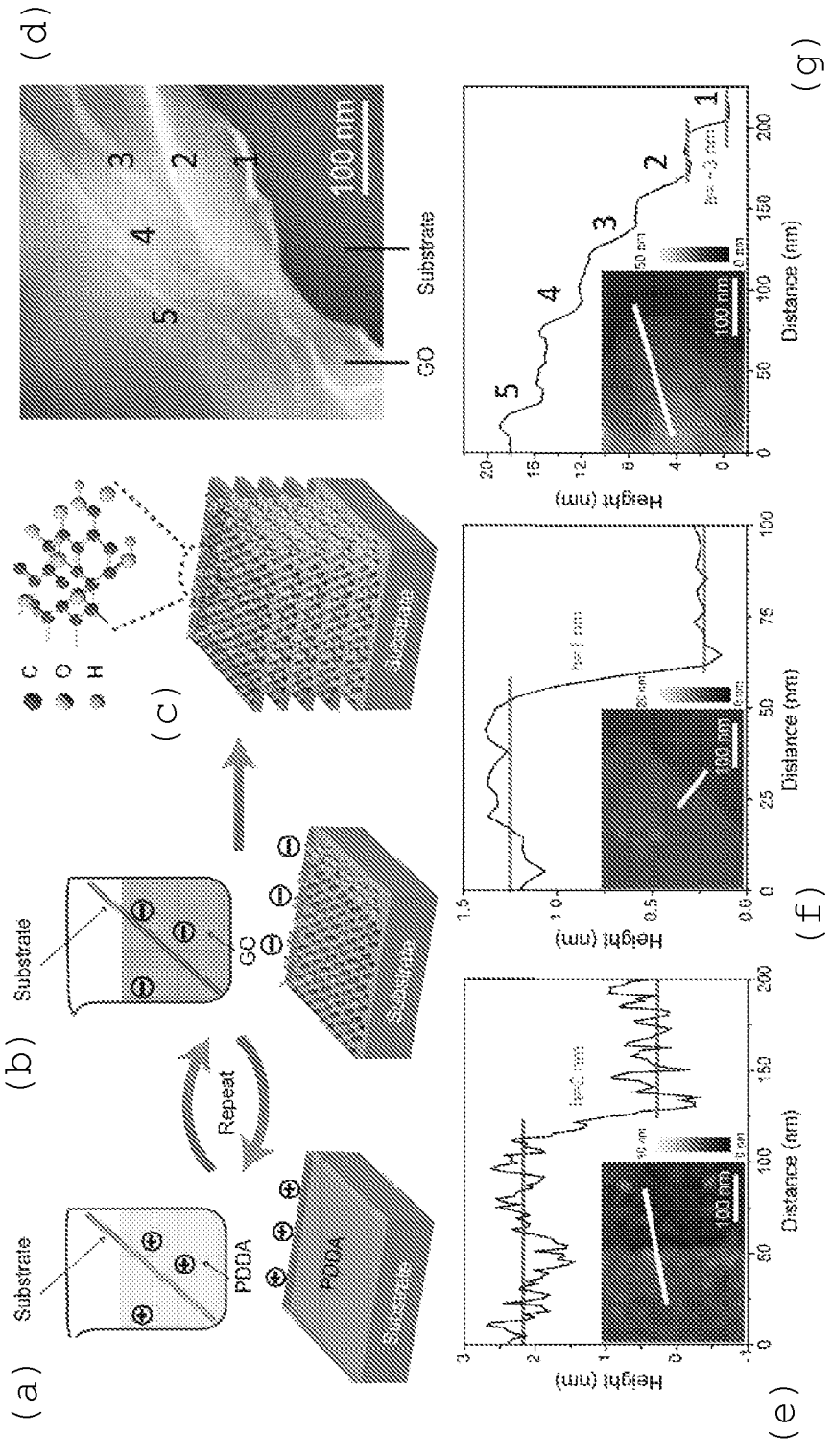
FIG. 14(a) shows one step of a process of fabrication of a graphene oxide film in accordance with an embodiment of the present invention.
FIG. 14(b) shows a further step of the process of fabrication of a graphene oxide film in accordance with the embodiment of FIG. 14(a)
FIG. 14(c) shows another step of the process of fabrication of a graphene oxide film in accordance with the embodiment of FIGS. 14(a) and 14(b)
FIG. 14(d) shows a scanning electron microscope image of a formed graphene-based metamaterial.
FIGS. 14(e)-(g) show images obtained by atomic force microscopy of a multi-layer graphene oxide film formed in accordance with the embodiment of FIGS. 14(a)-(d)
Figure 15:
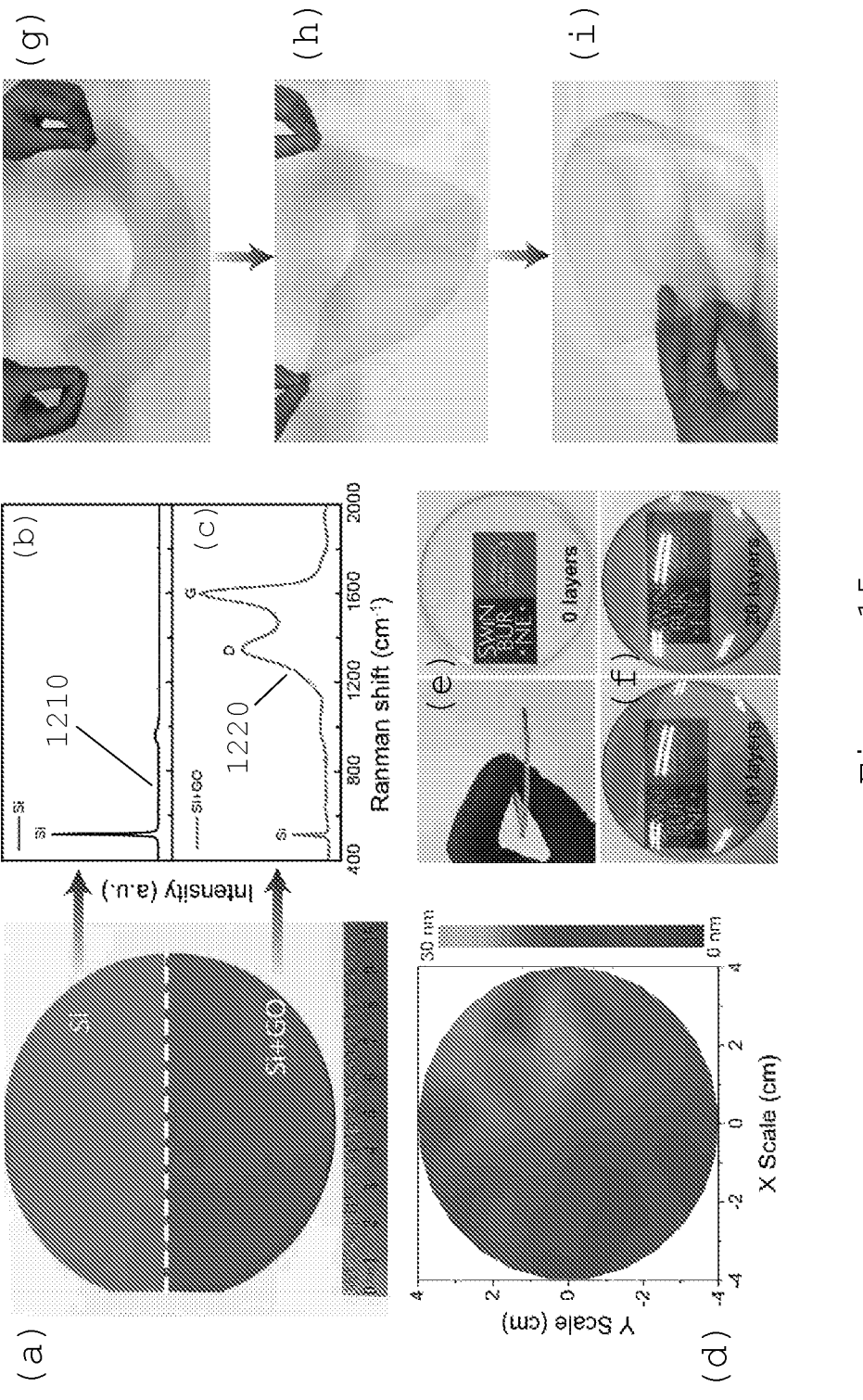
FIGS. 15(a)-(i) illustrate a further method of formation of an optical element comprising a graphene lens in accordance with a further embodiment of the present invention.
Figure 16:
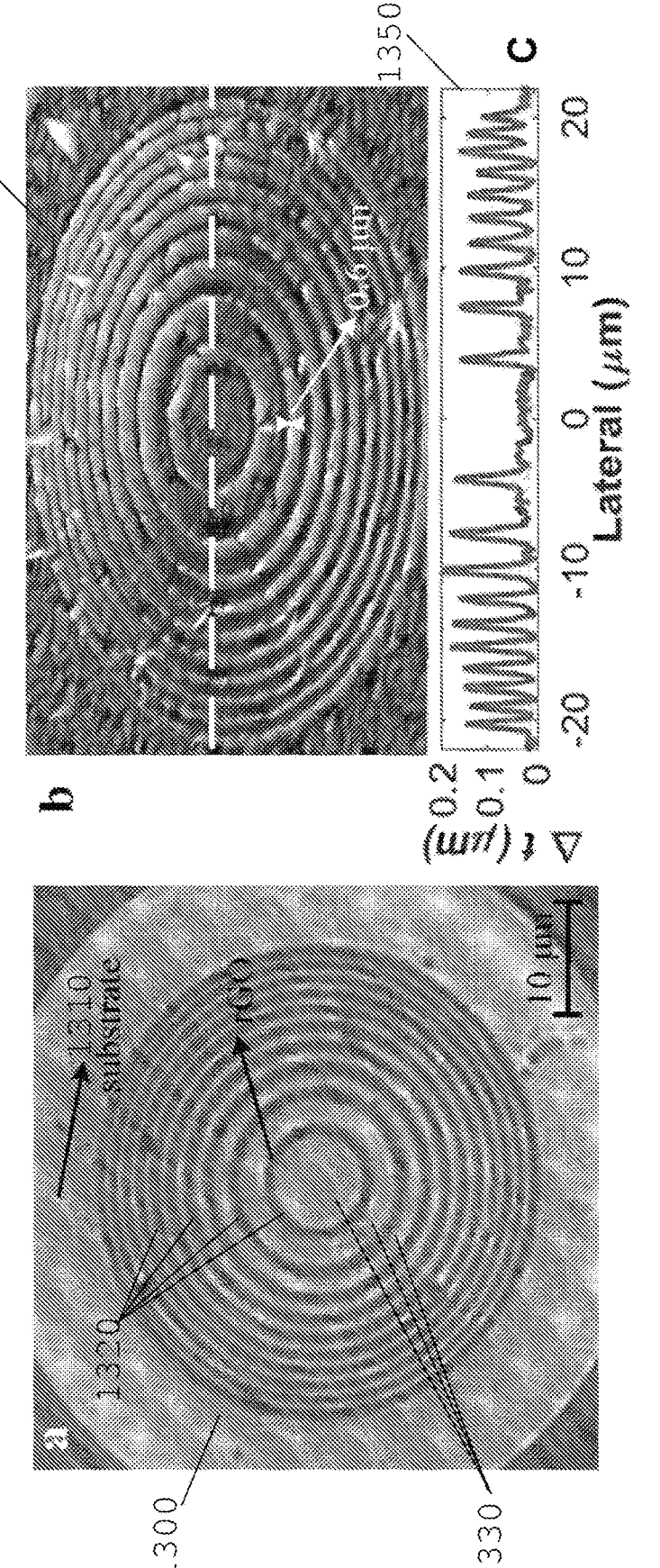
FIG. 16(*c*) depicts a cross-sectional profile of the graphene lens of FIG. 16(*a*)

FIGS. 13(a)-(d) show graphs 1010, 1020, 1030, 1040, and respective atomic force microscope (AFM) images 1050, 1060, 1070, 1080 of the GO films of FIG. 12, the thicknesses being 40 nm, 70 nm, 160 nm and 200 nm, respectively.

Self-Assemble Method

The self-assemble method allows producing very smooth and thin GO films on different substrates. The self-assemble method relies on the fact that GO flakes are negatively charged compounds and thus can be attracted to surfaces that are positively charged. Such surfaces may be provided by polymers comprising positively charged material. The fabrication process in the self-assemble method is illustrated schematically in FIG. 14.

A solution of positively charged dielectric material polyelectrolyte polydiallyldimethylammonium chloride (PDDA), which has low absorption and refractive index of ~1.5 from visible to near infrared wavelength, was used to attach to a substrate such that the substrate has a positively charged surface, as illustrated in FIG. 14(a). The substrate with the positively charged surface was then introduced into a solution of GO comprising the negatively charged GO flakes, as illustrated in FIG. 14(b), whereby a layer of GO was formed onto the positively charged surface of the substrate. By carefully controlling flake number, flake sizes and the concentration of the GO solution, a monolayer GO film can be formed, as seen in FIG. 14(b).

Repeating the PDDA and GO deposition process and as illustrated in FIG. 14(c), multiple layers of GO films can further be formed on the substrate with the thickness of each layer and the number of layers being carefully and precisely controlled. The morphology properties of the achieved graphene-based metamaterial can then be characterized by a scanning electron microscope (SEM) and an AFM. An SEM image of the formed graphene-based metamaterial is shown in FIG. 14(d), in which five ultrathin layers of GO films (PDDA-GO layers) can be identified. As illustrated in FIG. 14(e), the thickness of a monolayer of positively charged PDDA is ~2 nm as measured by AFM.

FIG. 14(f) illustrates that the thickness of a monolayer of negatively charged GO solution is ~1 nm as measured by AFM and FIG. 14(g) illustrates that each layer of GO film (couple PDDA-GO) is approximately 3 nm thick, which results in an overall thickness of 18 nm for a 5-layer GO film structure.

Further, to demonstrate the capability of large-scale fabrication of the method, a 5-layer GO film was coated on a 4-inch silicon wafer, as illustrated in FIG. 15(a) and the integration of the GO film on the silicon substrate was confirmed by a Raman spectroscopic measurement. FIG. 15(b) shows a Raman spectroscopic measurement 1210 for a silicon wafer and FIG. 15(c) shows the Raman spectroscopic measurement 1220 obtained for the silicon wafer coated with the GO film. The Raman spectroscopic measurement 1220 comprises two peaks D (at 1345 cm$^{-1}$) and G (at 1590 cm$^{-1}$) which are characteristic of GO. The D to G intensity ratio has a value of 0.7, which is indicative of a low defect density in the GO layers.

The thickness mapping of the 5-layer GO film illustrated in FIG. 15(d) demonstrates that the thickness is controlled at 18±1.5 nm over the entire wafer area, which approaches the accuracy of the state-of-the-art vacuum film deposition method. In addition, lenses having a curved surface are commonly challenging to coat uniformly by vacuum coating methods. However, the solution-based self-assemble method in accordance with the present embodiment of the present invention allows a direct coating of GO on substrates with arbitrary shapes without transfer process.

For demonstration, there is shown in FIG. 15(e) a 72-mm optical acrylic lens 1230 with a curved surface, and in FIG. 15(f) the optical element 1240 comprising a uniform 10-layer (FIG. 15(f) left) and 20-layer (FIG. 15(f) right) GO film coated on the 72 mm curved optical acrylic lens 1130 with high transmission. Further, FIGS. 15(g)-(i) illustrate a metamaterial comprising a 5-layer GO film formed on a flexible transparent substrate being bent and twisted. After various bending and twisting, the metamaterial remains without any visible wrinkles and/or cracks, which demonstrates an excellent mechanical strength and flexibility.

ii) Conversion of the GO Film into an RGO Film

As mentioned earlier, the graphene lens provided in accordance with embodiments of the present invention comprises concentric rings including graphene zones and air zones. The graphene zones are composed of RGO and several methods for converting the GO film into an RGO film exist, including thermal, chemical, microwave, flash light, focused ion beam, and photo reduction methods, which result in the removal of oxygen functional groups in the GO film and recover the graphene network.

In one embodiment, the photo reduction method was used, wherein the GO film was exposed under ultraviolet light (Olympus U-UIS100HG, USH-102D, 100 W, 200-600 nm wavelength) for three hours to form the RGO film.

iii) Laser Ablation of the RGO Film to Create the Graphene Lens

The concentric rings of the graphene lens are then formed using direct laser ablation. In the present embodiment, a femtosecond laser (Coherent®, Libra, λ=800 nm, pulse width=100 fs, repetition rate=10 kHz) was used, however any laser that allows providing power above an ablation threshold for the RGO film could be used.

FIG. 16(a) shows a transmission optical microscopic (50×) image of an example of a graphene lens 1300 fabricated in accordance with the self-assemble method on a substrate 1310. RGO zones or concentric rings 1320 can be clearly observed as well as the transparent or air zones 1330.

FIG. 16(b) shows the corresponding topographic profile 1340 of the graphene lens 1300 as measured by an optical profiler. FIG. 16(c) shows a cross-sectional profile 1350 of the graphene lens 1300 determined along the dashed line drawn on FIG. 16(b). It can be seen from the cross-sectional profile 1350 that each RGO ring has a profile that approximates a Gaussian profile, which is likely due to the Gaussian shaped focal spot of the laser beam used for the laser ablation step.

Figure 17:
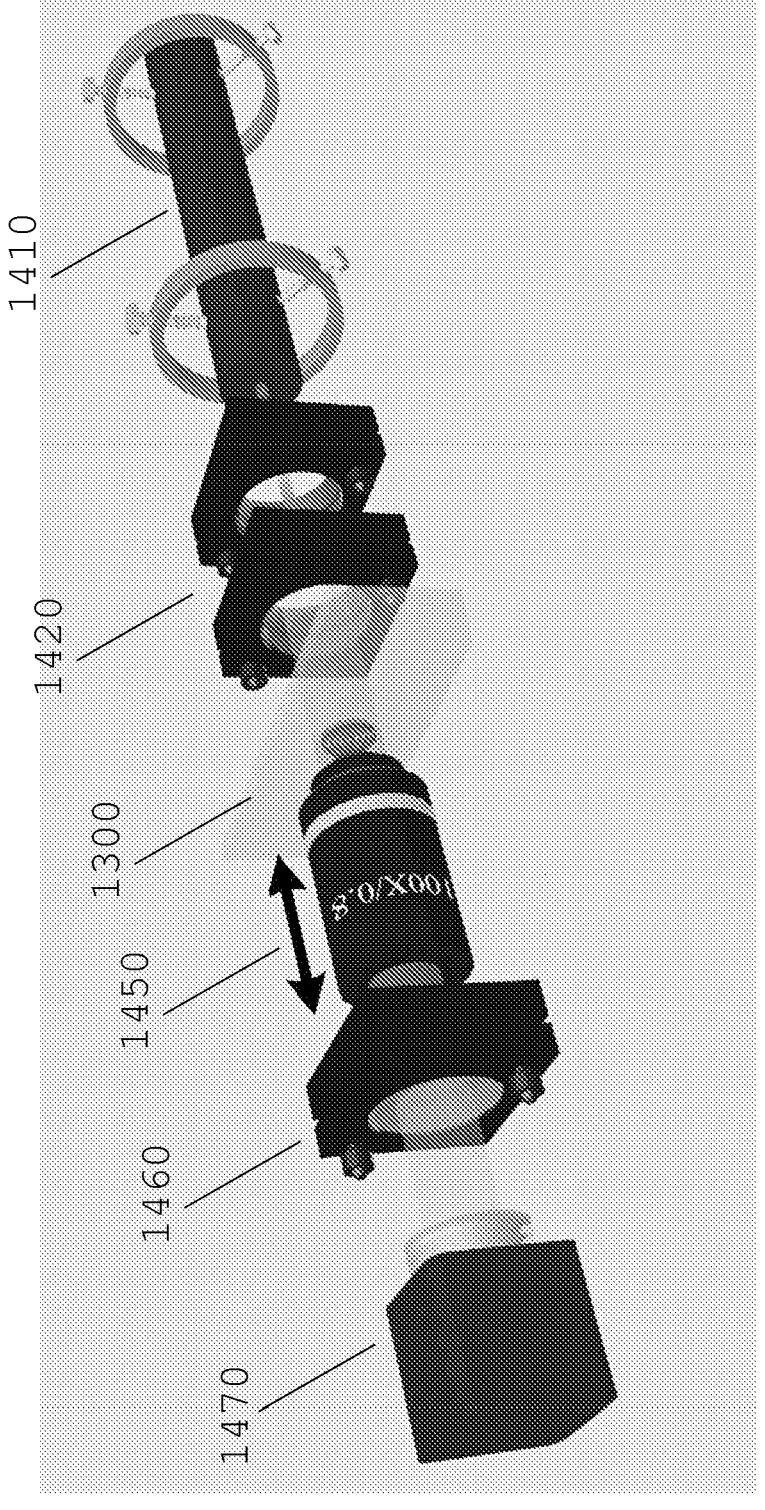
FIG. 17 shows an experimental set-up to measure the focal intensity distribution of a graphene lens in accordance with an embodiment of the present invention.

The focusing performance of the graphene lens 1300 is then typically tested using an experimental set-up such as the one illustrated schematically in FIG. 17, which allows measuring the focal intensity distribution of the graphene lens 1300. As seen in FIG. 17, the experimental set-up 1400 may comprise, for example, a source of electromagnetic radiation 1410 (e.g. laser) emitting a laser beam, and a beam expansion system (BES) 1420 composed of two lenses. The graphene lens 1300 is positioned in series with the BES 1420 and the source 1410 wherein the graphene lens 1300 is illuminated by the laser beam. The focal region or spot of the graphene lens 1300 is then imaged using an imaging system comprising an objective 1450 and lens 1460 and a further CCD camera 1470. The objective 1450 allows scanning the light transmitted by the graphene lens along the optical axis for recording the three-dimensional focal intensity distribution of the graphene lens 1300.

Figure 18:
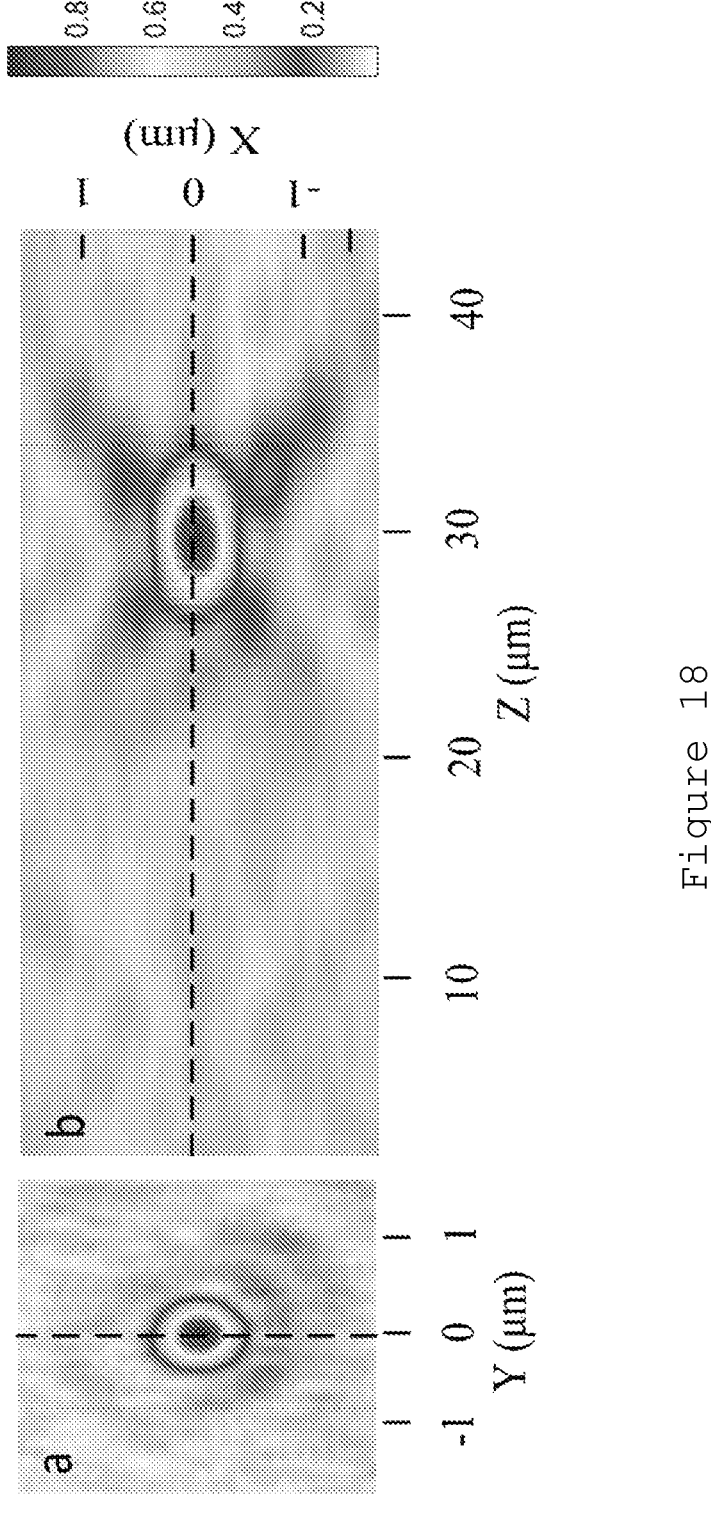
FIG. 18 shows two images of the focal intensity distribution of the graphene lens provided in accordance with an embodiment of the present invention (a) in the x-y focal plane and (b) in the x-z focal plane.

FIG. 18 shows two images of the focal intensity distribution 1500 of the graphene lens 1300 as imaged by the imaging system and CCD camera 1470(a) in the x-y focal plane and (b) in the x-z focal plane.

The fabricated graphene lens 1300 may then be further tested to ensure that it is suitable to resist various environments and in particular a harsh environment, in consideration of different types of applications, including a low Earth orbit condition (aerospace applications), strong acid and alkaline conditions (harsh chemical environment) and biochemical conditions (applications in living body conditions such as micro fibre endoscopy). For example, the test in a low Earth orbit condition typically includes a test for exposure of the graphene lens to extreme heat and cold cycles, strong UV radiation, ultrahigh vacuum, atomic oxygen, and high energy radiation. The National Aeronautics and Space Administration standard for the low Earth orbit condition may in particular be used. Testing and qualification of graphene lenses exposed to these extreme conditions can provide data to enable the manufacturing of long-life reliable graphene lenses used on Earth as well as in the sophisticated satellite and spacecraft components.

Testing of the graphene lenses under various harsh conditions indicate that they perform well and preserve their focal qualities under extreme ultraviolet radiation, extreme heat and cold, ultra-high vacuum, strong corrosive (acidic or alkaline) conditions and in biochemical environments. Under high atomic oxygen radiation conditions (typically experienced in low Earth orbital regions), the radiation exposure acts to reduce the thickness of graphene lenses over time. However, the graphene lenses were found to maintain good focal qualities during thickness changes and until the graphene layers are etched off by radiation. As such, graphene lenses used in applications to be subject to atomic oxygen radiation should be manufactured with a larger thickness to increase their operational lifetime.

FIG. 19 is a flow chart of a method 1600 of forming an optical device that is arranged to emit electromagnetic radiation, such as optical device 100, 140, 200 or 240. At step 1620, the method 1600 comprises providing an optical fibre for transmitting electromagnetic radiation between a source of electromagnetic radiation and an area of interest of a sample material.

Step 1620 involves preparing a flat tip of the optical fibre. This may be achieved by conventional fibre cleaving techniques such as suing a fibre cleaver (e.g. F-CLX-8 from the Newport Corporation)

At step 1640, the method 1600 comprises coupling an optical element comprising a graphene lens, such as graphene lens 300 or 1300, to an end portion of the optical fibre in a manner such that, in use, electromagnetic radiation transmitted by the optical fibre through the graphene lens is focused to a focal region within the area of interest of the sample material.

The optical device so formed is, in a particular embodiment, an endoscope and the sample material is a biological tissue. However, as mentioned earlier, it is envisaged that any other suitable sample material may be considered.

At step 1640, the optical element comprising the graphene lens can be formed indirectly onto the end portion or end tip of the optical fibre using, for example, the vacuum filtration method described above with reference to FIG. 11, or the self-assemble method described above with reference to FIGS. 14 to 16. Using the self-assemble method, a substrate is attached or formed directly onto the end portion or end tip of the optical fibre and a GO film is formed onto the substrate at the end portion of the optical fibre as described above. The GO film may then be first photo reduced under UV light to form an RGO film, and the RGO film is then laser ablated to form the concentric rings of the graphene lens. The substrate may be a silicon wafer or may be a glass substrate.

The optical element comprising the graphene lens may alternatively be formed (using the vacuum filtration method or the self-assemble method) and then provided and attached to the end portion of the optical fibre. In this embodiment, the substrate or at least a portion of the substrate with the formed optical element can be attached to the end portion of the optical fibre. In some cases, to improve the success rate of coupling, it may be preferably to keep the GO film moist before it is transferred onto the fibre tip.

It will also be understood that the optical element with the graphene lens may alternatively be removed, for example, chemically removed, from the substrate, wherein the removed optical element can then be provided and attached to the end portion of the optical fibre to form the optical device.

When attaching the optical element to the end portion of the optical fibre, the optical element is positioned relative to the end portion of the optical fibre such that the graphene lens covers a core of the optical fibre, i.e. as described with reference to FIGS. 1 and 2, the graphene lens preferably overlaps with the fibre core to ensure an optimal optical focusing performance of the optical device.

In order to ensure that the graphene lens is well overlap with the optical fibre core, a laser beam is coupled into the optical fibre core as an illumination. An image in the focal plane of the graphene lens is then acquired, wherein if the graphene lens is well overlap with the optical fibre core, a focal spot having the diameter of the graphene lens and in which the concentric rings of the graphene lens can be observed should be observed. FIG. 20(a) shows an image 1700 obtained as the laser beam is transmitted by an optical fibre core having a diameter of 6 □m through a graphene lens having the same diameter, i.e. 6 □m also. The focal spot 1720 is observed having a diameter of about 6 □m, and the concentric rings of the graphene lens can be clearly observed. FIG. 20(b) shows an image 1740 obtained as no light is coupled into the optical fibre core. The focal spot having a diameter of 6 □m can still be observed, however in a less clear manner.

Thus, the optical device provided in accordance with embodiments of the present invention can have a substantially smaller size as compared to commonly existing optical fibre probes or endoscopes while allowing to achieve a substantially improved sub-micron optical resolution.

The optical device provided in accordance with embodiments of the present invention is typically further arranged to receive electromagnetic radiation that interacted with the area of interest of the sample material. In the particular application, wherein the optical device is an endoscope, or also in the particular application wherein the optical device forms part of an OCT system, images from the area of interest of the sample material can thus be acquired.

The graphene lens is thus arranged to receive electromagnetic radiation that interacted with the area of interest of the sample material and the optical fibre is further arranged to transmit the electromagnetic radiation received by the optical element to an optical system for processing/imaging.

Figure 21:
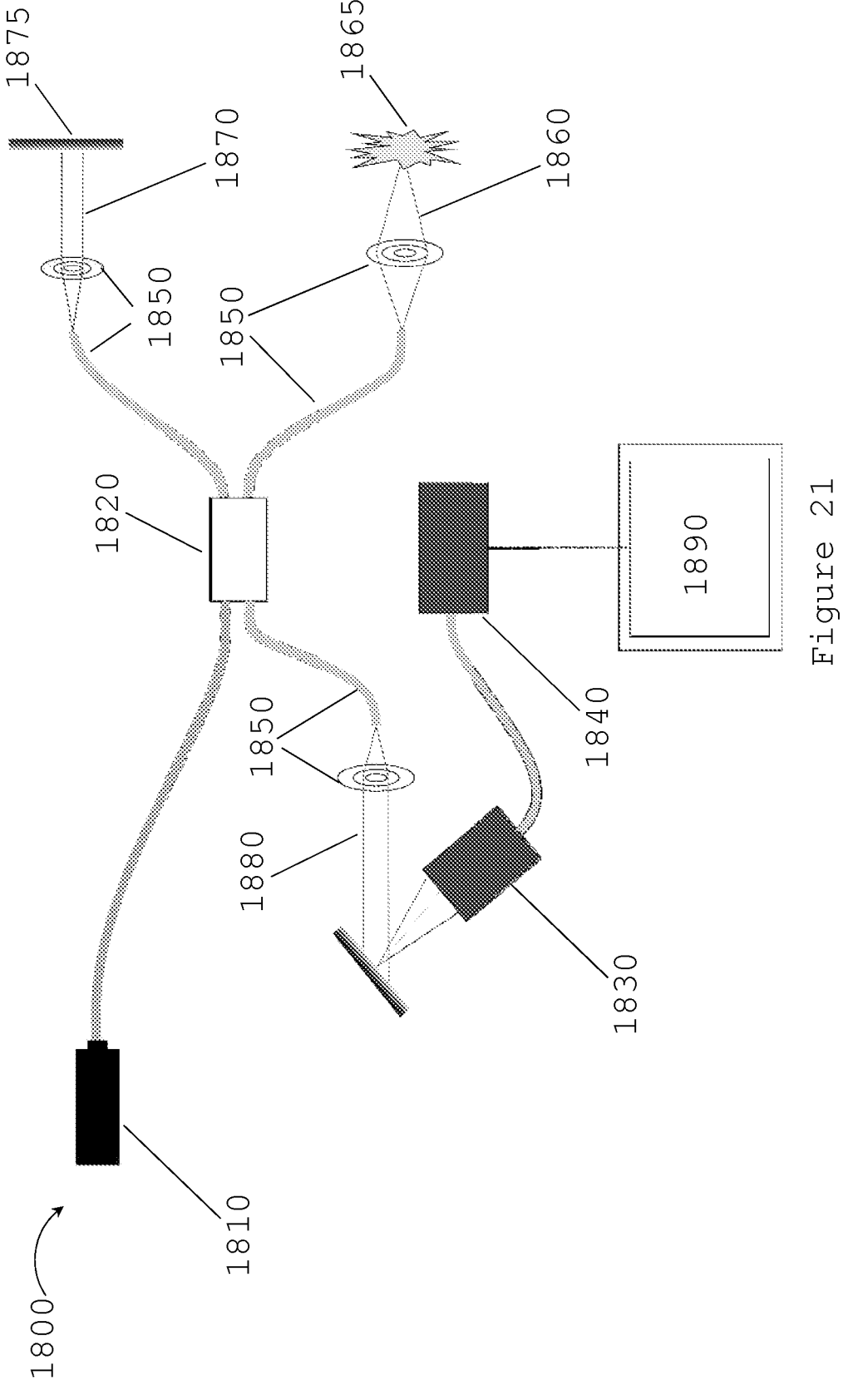
FIG. 21 shows a schematic representation of an OCT imaging system comprising the optical device in accordance with an embodiment of the present invention.

FIG. 21 shows a schematic representation of an OCT imaging system 1800 comprising a source of electromagnetic radiation 1810, a beam splitter 1820, a detector 1830, a digital signal processing system 1840, and an optical device 1850 provided in accordance with embodiments of the present invention. The optical element of optical device 1850 comprising the graphene lens provided in accordance with embodiments of the present invention can be provided in the OCT imaging system 1800 to modulate the beam of electromagnetic radiation 1860 directed to and received from an area of interest of a sample material 1865, to modulate a reference beam 1870 directed to and received from a reference area of a reference material 1875, as well as to modulate the beam of electromagnetic radiation 1880 that interacted with both the reference area of the reference material and the area of interest of the sample material. The OCT imaging system 1800 typically further comprises a graphical user interface 1890 wherein an OCT image can be obtained.

Figure 22:
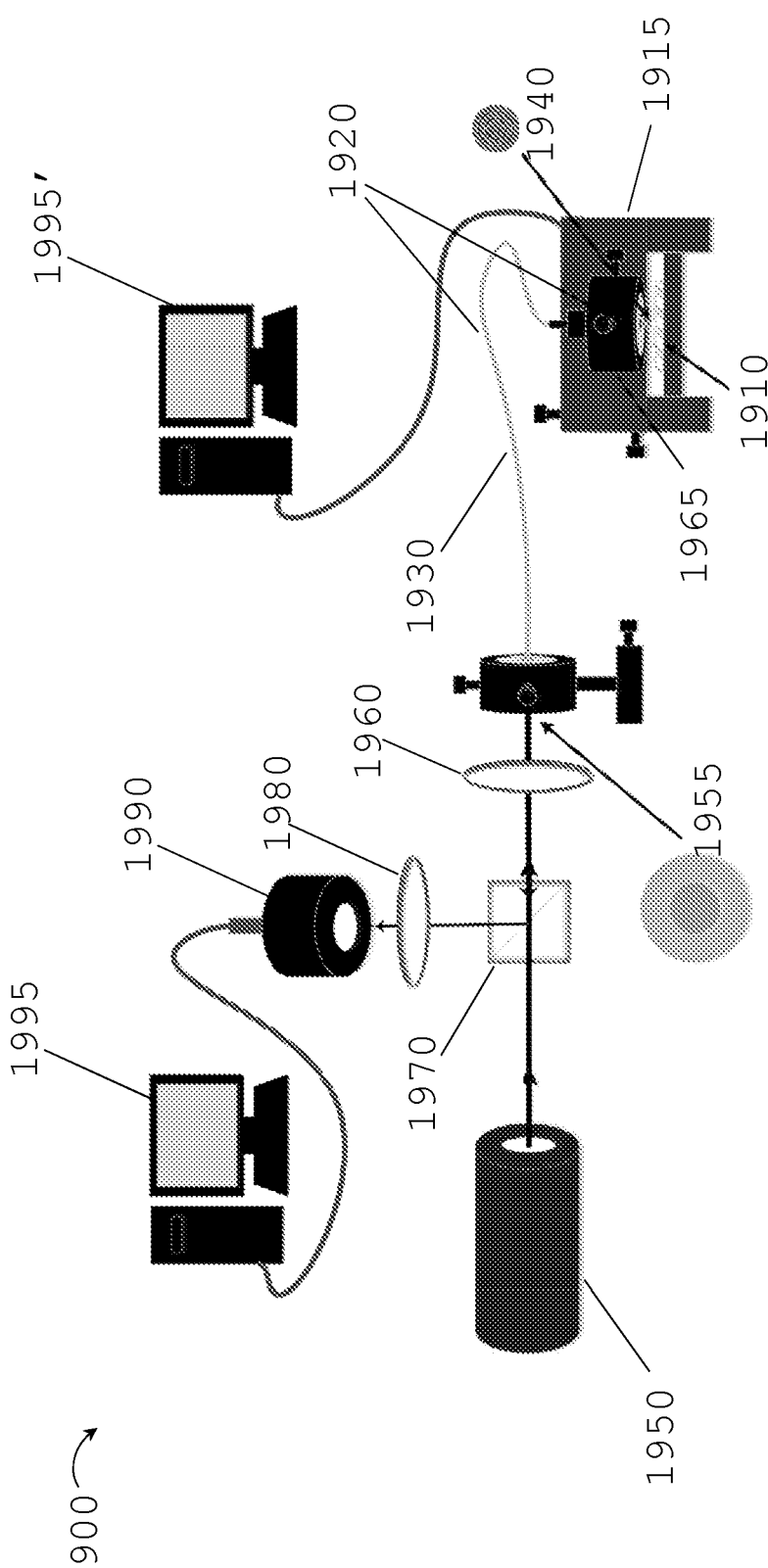
FIG. 22 illustrates a scanning imaging system comprising an optical device in accordance with an embodiment of the present invention.

FIG. 22 illustrates a scanning imaging system 1900 that can be used to image an area of interest of a sample material 1910. The scanning imaging system 1900 comprises an optical device 1920 comprising an optical fibre 1930 and an optical element comprising a graphene lens 1940 coupled to an end portion or tip of the optical fibre 1930. The optical device 1920 is provided in accordance with the described embodiments of the present invention.

A source of electromagnetic radiation 1950 is provided and a laser beam is thus focused onto the flat tip side 1955 of the optical fibre 1930 by means of a lens 1960. The graphene lens 1940 is coupled to the other tip of the optical fibre 1930 so as to focus the electromagnetic radiation or laser beam to a focal region of the area of interest of the sample material 1910 held onto an electronic scanning platform 1915.

The scanning imaging system also comprises a scanning head 1965 that is coupled to, or comprises at least a portion of, the optical device 1920, the scanning head 1965 being arranged for changing a position of the optical element (and graphene lens 1940) of the optical device 1920 relative to the sample material 1910 such that the focal region within the area of interest can be scanned across the area of interest of the sample material 1910.

Light that interacted with the area of interest is then received by the graphene lens 1940 and may comprise light that reflected at a surface of the area of interest and/or fluorescence emitted by the surface of the area of interest. The reflected light and/or fluorescence are then transmitted by the optical fibre 1930 and refracted by a beam splitter 1970 to go through a lens 1980 and collected by a CCD camera 1990.

The collected light can then be imaged onto a graphical user interface 1995. As a position of the optical element and graphene lens 1940 is changed by means of the scanning head, the focal region is scanned across the area of interest of the sample material 1910 and an image of the area of interest can be obtained, whereby the area of interest of the sample material can be characterised. A further graphical user interface 1995' may further be provided directly connected to the electronic scanning platform 1915 holding the sample material 1910 for monitoring directly the positioning of the scanning head 1965 relative to the area of interest of the sample material 1910.

Figure 23:
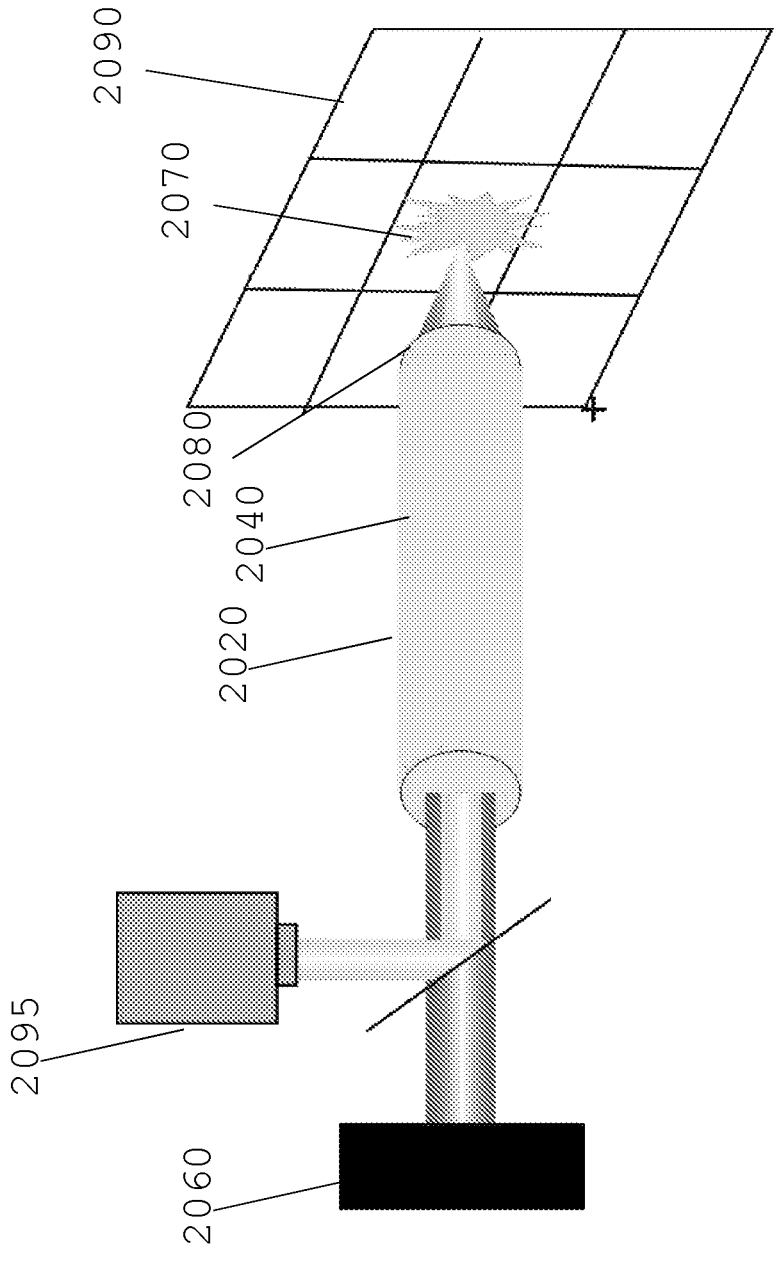
FIG. 23 illustrates a scanning imaging system comprising an optical device in accordance with a further embodiment of the present invention.

FIG. 23 illustrates a further scanning imaging system 2000 comprising an optical device 2020 in which the optical fibre 2040 is a multi-mode fibre, and a spatial light modulator 2060. Spatial light modulator 2060 is coupled to the optical device 2020 and is arranged for phase modulation of the electromagnetic radiation transmitted through the optical fibre 2040. The spatial light modulator 2060 allows the optical device 2020 to scan the focal region 2070 (focused by the graphene lens 2080 of the optical device 2020 on the area of interest 2090 of the sample material) across the area of interest 2090 by phase modulation of the different modes of the multi-mode optical fibre 2040.

Light reflected at the focal region of the area of interest and/or fluorescence emitted at the focal region of the area of interest 2090 are then received by the graphene lens 2080 and transmitted through the optical fibre 2040 towards a detector 2095 for subsequent imaging.

In the embodiment wherein the optical fibre is one of a bundle of optical fibres and the optical element comprising the graphene lens is coupled to the end portions of the optical fibres of the bundle, the electromagnetic radiation that interacted with the area of interest of the sample material and is received by the graphene lens can directly be imaged onto the fibre bundle.

Figure 24:
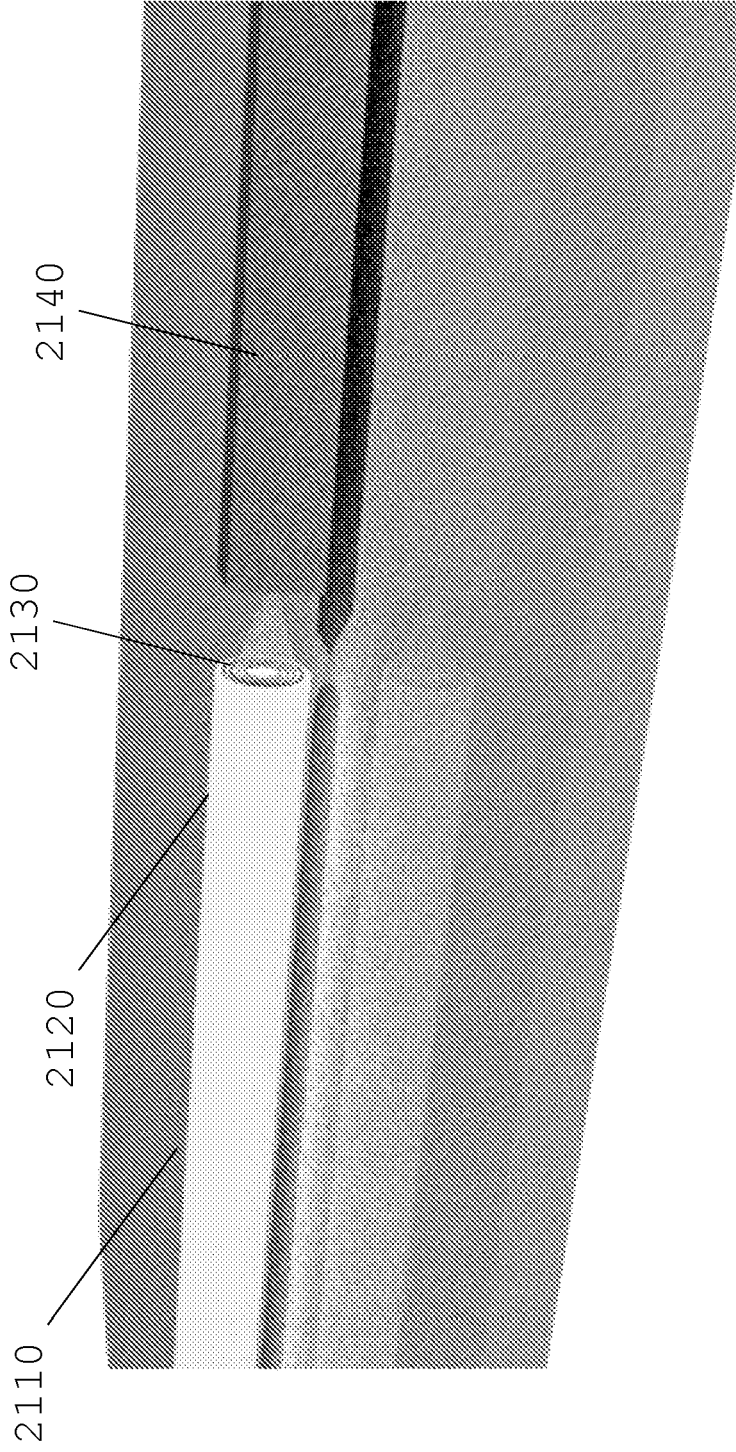
FIG. 24 shows an optical device in accordance with a further embodiment of the present invention.

In a further embodiment illustrated in FIG. 24, the optical device provided in accordance with embodiments of the present invention can further be used for other applications such as to allow the coupling of light into a photonic chip. An optical device 2110 is shown comprising an optical fibre 2120 and an optical element comprising a graphene lens 2130 wherein light emitted by the optical device 2110 is to be coupled into a photonic chip 2140. The optical device 2110 in this embodiment typically corresponds to an optical fibre coupler.

The optical devices described above utilise graphene lenses and provide improved resolution at substantially smaller sizes as compared to commonly known devices. These improvements are particularly advantageous in optical fibre probes or endoscopes to provide improved imaging while reducing the invasiveness of the instrument to a patient.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features in various embodiments of the invention.

Modifications and variations as would be apparent to a skilled addressee are determined to be within the scope of the present invention.

It is also to be understood that, if any prior art publication is referred to herein, such reference does not constitute an admission that the publication forms a part of the common general knowledge in the art, in Australia or any other country.

The invention claimed is:

1. An optical device that is arranged to emit electromagnetic radiation, the optical device comprising:
    an optical fibre that is arranged to transmit electromagnetic radiation between a source of electromagnetic radiation and an area of interest of a sample material; and
    an optical element formed directly on an end-portion of the optical fibre, the optical element comprising a graphene lens having a plurality of concentric rings disposed over a core of the optical fibre and having radii determined based on electric field modes of the optical fibre, wherein the graphene lens has a diameter that is substantially matched with a diameter of the optical fibre core, and that is arranged to focus the electromagnetic radiation transmitted by the optical fibre to a focal region within the area of interest of the sample material.

2. The optical device of claim 1, wherein the optical device is further arranged to receive electromagnetic radiation that interacted with the area of interest of the sample material.

3. The optical device of claim 2, wherein the optical element is arranged to receive electromagnetic radiation that interacted with the area of interest of the sample material and the optical fibre is further arranged to transmit the electromagnetic radiation received by the optical element.

4. The optical device of claim 1, wherein the optical fibre comprises a multi-mode optical fibre and the optical element comprises at least two graphene lenses that are arranged to focus light transmitted by the optical fibre to at least two focal regions within the area of interest of the sample material.

5. The optical device of claim 1, wherein the optical fibre is one optical fibre of a bundle of optical fibres and the optical element is one optical element of a plurality of optical elements.

6. The optical device of claim 5, wherein each optical element of the plurality of optical elements is formed directly on an end-portion of a respective one optical fibre of the bundle of optical fibres.

7. The optical device of claim 1, wherein the optical device comprises a bundle of optical fibres, the optical element being formed directly on end portions of the optical fibres of the bundle of optical fibres.

8. The optical device of claim 1, wherein the graphene lens is arranged to focus the electromagnetic radiation to the focal region with a sub-micron optical resolution.

9. An endoscope comprising the optical device of claim 1.

10. An optical coherence tomography system comprising the optical device of claim 1.

11. A scanning imaging system comprising:
the optical device of claim 1; and
a scanning head coupled to, or comprising at least a portion of, the optical device, the scanning head being arranged for changing a position of the optical element of the optical device relative to the sample material such that the focal region within the area of interest can be scanned across the area of interest of the sample material.

12. A scanning imaging system comprising:
the optical device of claim 1; and
a spatial light modulator coupled to the optical device, the spatial light modulator being arranged for phase modulation of electromagnetic radiation transmitted through the optical fibre;
wherein the optical device is arranged to scan the focal region across the area of interest by phase modulation;
wherein the optical fibre comprises a bundle of multi-mode optical fibre and the optical element is formed directly on the end portions of the optical fibres of the bundle of multi-mode optical fibre; and
wherein the optical element comprises at least two graphene lenses that are arranged to focus light transmitted by the optical fibre to at least two focal regions within the area of interest of the sample material.

13. The scanning imaging system of claim 12, wherein the scanning imaging system further comprises a scanning head coupled to, or comprising at least a portion of, the optical device, the scanning head being arranged for changing a position of the optical element relative to the sample material such that the focal region can be scanned across another adjacent area of interest of the sample material.

14. An optical fibre coupler for coupling light into a photonic chip, the optical fibre coupler comprising the optical device of claim 1.

15. The optical device of claim 1, wherein the graphene lens comprises 3 to 10 concentric rings.

16. The optical device of claim 15, wherein an innermost concentric ring of the 3 to 10 concentric rings has a radius in a range of 1.2 to 7 microns.

17. The optical device of claim 15, wherein an outermost concentric ring of the 3 to 10 concentric rings has a radius in a range of 3 to 36 microns.

18. The optical device of claim 1, wherein the graphene lens is configured to focus the electromagnetic radiation to a focal length between 1.7 and 2.0 microns for a single mode fibre.

19. The optical device of claim 1, wherein the graphene lens is configured to focus the electromagnetic radiation to a focal length between 50 and 100 microns for a multimode fibre.

20. A method of forming an optical device that is arranged to emit electromagnetic radiation, the method comprising:
providing an optical fibre for transmitting electromagnetic radiation between a source of electromagnetic radiation and an area of interest of a sample material; and
forming an optical element comprising a graphene lens directly on an end portion of the optical fibre in a manner such that, in use, electromagnetic radiation transmitted by the optical fibre through the graphene lens is focused to a focal region within the area of interest of the sample material;
wherein the graphene lens has a plurality of concentric rings disposed over a core of the optical fibre and having radii determined based on electric field modes of the optical fibre, wherein the graphene lens has a diameter that is substantially matched with a diameter of the optical fibre core
wherein the graphene lens has a diameter that is substantially matched with a diameter of the optical fibre core, and wherein the graphene lens.

21. The method of claim 20, wherein the step of forming the optical element directly on the end portion of the optical fibre comprises positioning the optical element relative to the end portion of the optical fibre such that the graphene lens covers a core of the optical fibre.

* * * * *